United States Patent
Taylor et al.

(10) Patent No.: US 6,664,400 B2
(45) Date of Patent: Dec. 16, 2003

(54) N-ARYLSULFONAMIDE AND PYRROLIDINECARBOXYLIC ACID INTERMEDIATES, AND THEIR USE FOR THE PREPARATION OF HERBICIDAL 1,3-DIOXO-1H-PYRROLO[1,2-C]IMIDAZOLE DERIVATIVES

(75) Inventors: Eric Deguyon Taylor, Wilmington, DE (US); Viacheslav Alexandrovich Petrov, Hockessin, DE (US); Matthias Schaeffer, Goldbach (DE); Karlheinz Drauz, Freigericht (DE); Anne Vogt, Hanau (DE); Christoph Weckbecker, Hanau (DE); Steven H. Swearingen, Wilmington, DE (US); Balreddy Kamireddy, Hockessin, DE (US)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 10/035,136

(22) Filed: Jan. 4, 2002

(65) Prior Publication Data
US 2002/0137946 A1 Sep. 26, 2002

Related U.S. Application Data

(62) Division of application No. 09/367,899, filed as application No. PCT/US98/02721 on Feb. 13, 1998, now Pat. No. 6,384,234.
(60) Provisional application No. 60/038,429, filed on Feb. 19, 1997.

(51) Int. Cl.⁷ .................. C07D 207/12; A01N 43/36
(52) U.S. Cl. ....................... 548/538; 504/287
(58) Field of Search ................. 504/287; 548/538

(56) References Cited

U.S. PATENT DOCUMENTS 3,639,474 A    2/1972    Harrington et al. ......... 260/556

FOREIGN PATENT DOCUMENTS

| JP | WO96/20195 | 7/1996 |
|----|------------|--------|
| WO | WO96/36615 | 11/1996 |
| WO | WO97/15576 | 5/1997 |

*Primary Examiner*—Taofiq Solola
(74) *Attorney, Agent, or Firm*—Oblon, Spivak, McClelland, Maier & Neustadt, P.C.

(57) ABSTRACT

The present invention relates to a compound of Formula 3

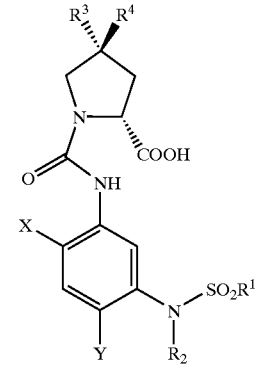

wherein
- X is H, F or Cl;
- Y is F or Cl;
- $R^1$ is $C_1$–$C_3$ haloalkyl, $C_2$–$C_4$ alkoxyalkyl; $C_2$–$C_6$ haloalkoxyalkyl or $C_2$–$C_6$ cyanoalkyl;
- $R^2$ is H, $C_1$–$C_4$ alkyl, $C_1$–$C_4$ haloalkyl, $C_3$–$C_4$ alkenyl, $C_3$–$C_4$ alkynyl, $C_2$–$C_4$ alkoxyalkyl, $C_2$–$C_4$ alkylcarbonyl or $C_2$–$C_4$ alkoxycarbonyl;
- $R^3$ is H or OH; and
- $R^4$ is H, F or Cl;
- provided that when $R^3$ is H then $R^4$ is F or Cl and when $R^3$ is OH then $R^4$ is H.

24 Claims, No Drawings

N-ARYLSULFONAMIDE AND PYRROLIDINECARBOXYLIC ACID INTERMEDIATES, AND THEIR USE FOR THE PREPARATION OF HERBICIDAL 1,3-DIOXO-1H-PYRROLO[1,2-C]IMIDAZOLE DERIVATIVES

This application is a Div. of application Ser. No. 09/367,899 filed Dec. 30, 1999 now U.S. Pat. No. 6,384,234 which is a 371 of PCT/US98/02721 filed Feb. 13, 1998, which claims benefit of application Ser. No. 60/038,429 filed Feb. 19, 1997.

BACKGROUND OF THE INVENTION

This invention pertains to compounds and processes which are useful for preparing herbicidal sulfonamides.

WO 95/27698-A1 discloses herbicidal sulfonamides for crop protection. There is a continuing need to develop compounds and processes useful for efficiently preparing these herbicidal sulfonamides.

SUMMARY OF THE INVENTION

This invention is directed to compounds and intermediates of Formulae 6 and 3, useful in preparing herbicidal sulfonamides of Formula 1, including all geometric and stereoisomers thereof, and agricultural salts thereof.

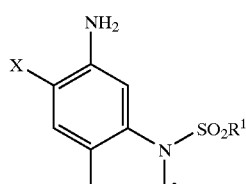
6

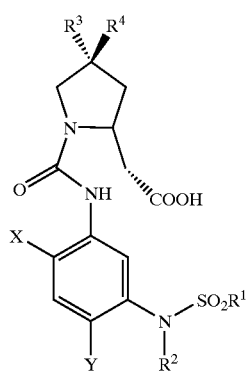
3

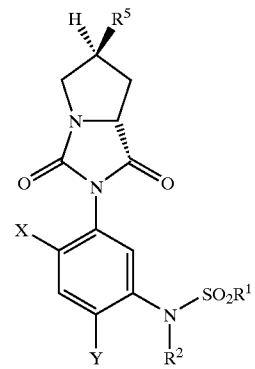
1 wherein
X is H, F or Cl;
Y is F or Cl;
$R^1$ is $C_1-C_3$ haloalkyl, $C_2-C_4$ alkoxyalkyl; $C_2-C_6$ haloalkoxyalkyl or $C_2-C_6$ cyanoalkyl;
$R^2$ is H, $C_1-C_4$ alkyl, $C_1-C_4$ haloalkyl, $C_3-C_4$ alkenyl, $C_3-C_4$ alkynyl, $C_2-C_4$ alkoxyalkyl, $C_2-C_4$ alkylcarbonyl or $C_2-C_4$ alkoxycarbonyl;
$R^3$ is H or OH;
$R^4$ is H, F or Cl; and
$R^5$ is F or Cl;
provided that when $R^3$ is H then $R^4$ is F or Cl and when $R^3$ is OH then $R^4$ is H.

This invention is further directed to a process for preparing a compound of Formula I

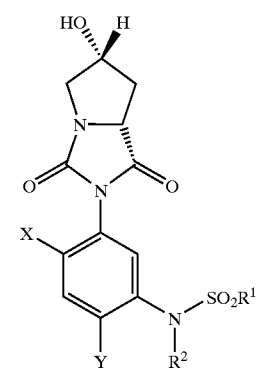
1 comprising halogenation of a compound of Formula 2a

2a wherein the substituents are as first defined in the Summary of the Invention.

This invention is further directed to a process for preparing a compound of Formula 2

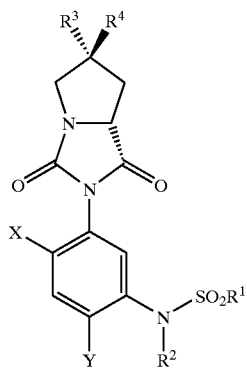

comprising cyclization of a compound of Formula 3

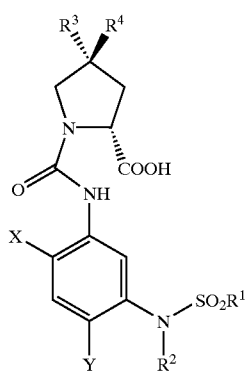

wherein the substituents are as first defined in the Summary of the Invention.

This invention is further directed to a process for preparing a compound of Formula 3

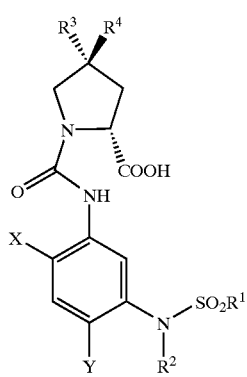

comprising reaction of a compound of Formula 5

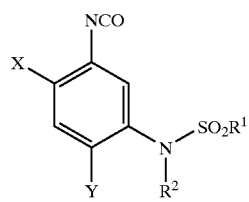

with a compound of Formula 4

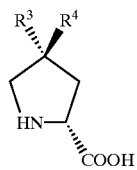

wherein the substituents are as first defined in the Summary of the Invention.

This invention is further directed to a process for preparing a compound of Formula 6

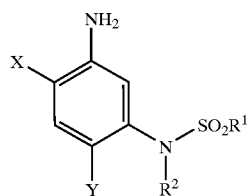

comprising a) reaction of a compound of Formula 8

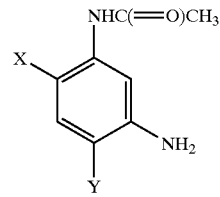

with a compound of formula $X^1SO_2R^1$ in the presence of a base to provide a compound of Formula 7;

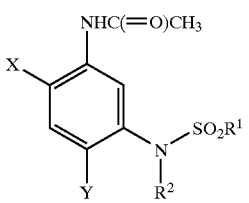

b) optional reaction of the compound of Formula 7 wherein $R^2$ is H with $X^1R^2$ in the presence of a base to provide a compound of Formula 7 wherein $R^2$ is other than H; and c) hydrolysis of the compound of Formula 7 with an acid or base to provide a compound of Formula 6;

wherein X¹ is halogen, $C_2$–$C_4$ alkylcarbonyloxy, $C_1$–$C_4$ alkoxy, phenoxy, cyano or imidazolyl, and the remaining substituents are as first defined in the Summary of the Invention.

This invention is further directed to a process for preparing a compound of Formula 6a

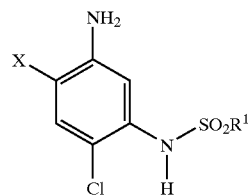

6a wherein a process sequence is selected from

A) a process sequence comprising a) reduction of a compound of Formula 12

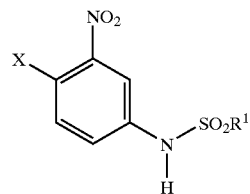

12 to provide a compound of Formula 11

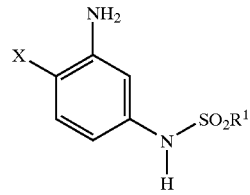

11 and b) chlorination of the compound of Formula 10 to provide a compound of Formula 6a;

wherein the substituents are as first defined in the Summary of the Invention; and B) a process sequence comprising a) reduction of a compound of Formula 15

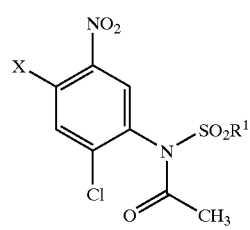

15 to provide a compound of Formula 14

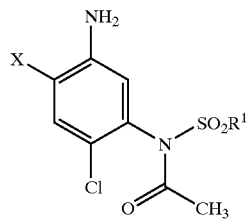

14 and b) hydrolysis of the compound of Formula 14 to provide a compound of Formula 6a;

wherein the substituents are as first defined in the Summary of the Invention.

This invention is further directed to a process for preparing a compound of Formula I

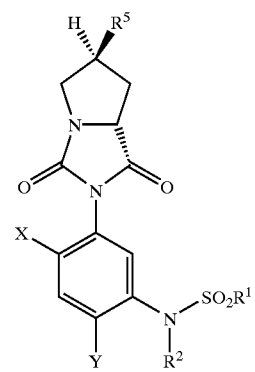

1 comprising a) cyclization of a compound of Formula 3

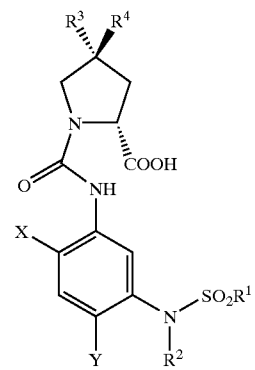

3 to provide the compound of Formula 2a

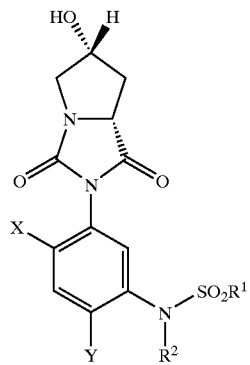

2a and b) halogenation of the compound of Formula 2a to provide a compound of Formula 1 wherein $R^3$ is OH, $R^4$ is H, and the remaining substituents are as first defined in the Summary of the Invention.

This invention is further directed to a process for preparing a compound of Formula 2

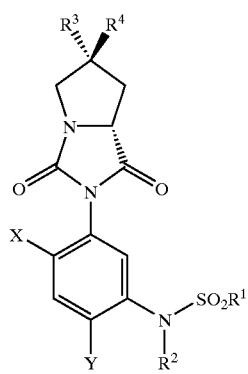

2 comprising a) reaction of a compound of Formula 5

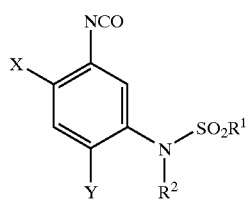

5 with a compound of Formula 4

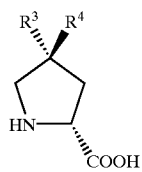

4 to provide the compound of Formula 3

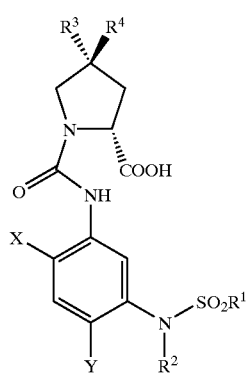

3 and b) cyclization of the compound of Formula 3 to a compound of Formula 2

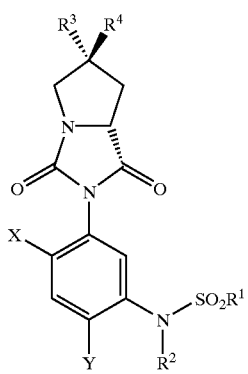

2 wherein the substituents are as first defined in the Summary of the Invention.

DETAILS OF THE INVENTION

This invention relates to compounds and intermediates for preparing herbicidal sulfonamides of Formula 1, including all geometric and stereoisomers thereof, and agricultural salts thereof.

The compounds and processes of this invention are illustrated below. The compounds of Formula 1 can be prepared via the processes of Steps 1–8 when $R^3$ is OH. Alternatively, the compounds of Formula 1 can also be prepared via the processes of Steps 1–7 when $R^4$ is F or Cl (compounds of Formula 2 wherein $R^4$ is F or Cl are the same as compounds of Formula 1).

Further embodiments of the present invention are the alternative processes for preparing compounds of Formula 6a, which can be prepared by the processes of Steps 9–11 or by the processes of Steps 12–16.

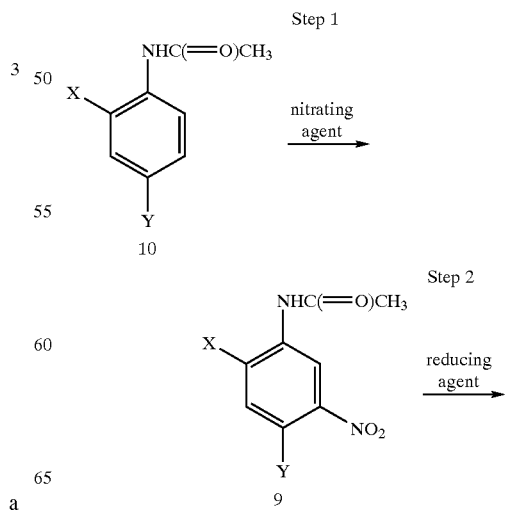

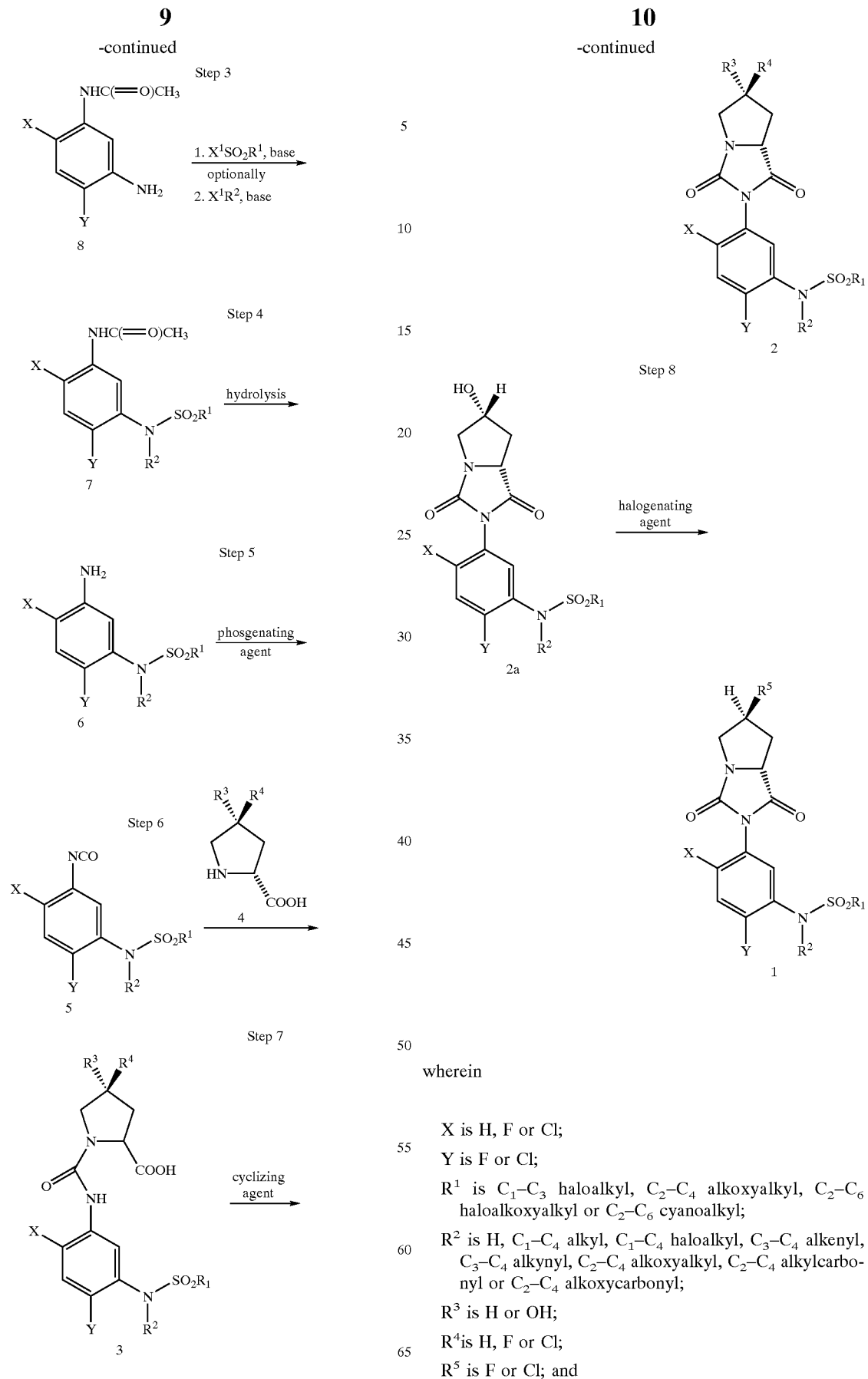
wherein
X is H, F or Cl;
Y is F or Cl;
$R^1$ is $C_1$–$C_3$ haloalkyl, $C_2$–$C_4$ alkoxyalkyl, $C_2$–$C_6$ haloalkoxyalkyl or $C_2$–$C_6$ cyanoalkyl;
$R^2$ is H, $C_1$–$C_4$ alkyl, $C_1$–$C_4$ haloalkyl, $C_3$–$C_4$ alkenyl, $C_3$–$C_4$ alkynyl, $C_2$–$C_4$ alkoxyalkyl, $C_2$–$C_4$ alkylcarbonyl or $C_2$–$C_4$ alkoxycarbonyl;
$R^3$ is H or OH;
$R^4$ is H, F or Cl;
$R^5$ is F or Cl; and $X^1$ is halogen, $C_2$–$C_4$ alkylcarbonyloxy, $C_1$–$C_4$ alkoxy, phenoxy, cyano or imidazolyl;

provided that when $R^3$ is H then $R^4$ is F or Cl and when $R^3$ is OH then $R^4$ is H.

Further processes of this invention to prepare intermediates of Formula 6a are illustrated below.

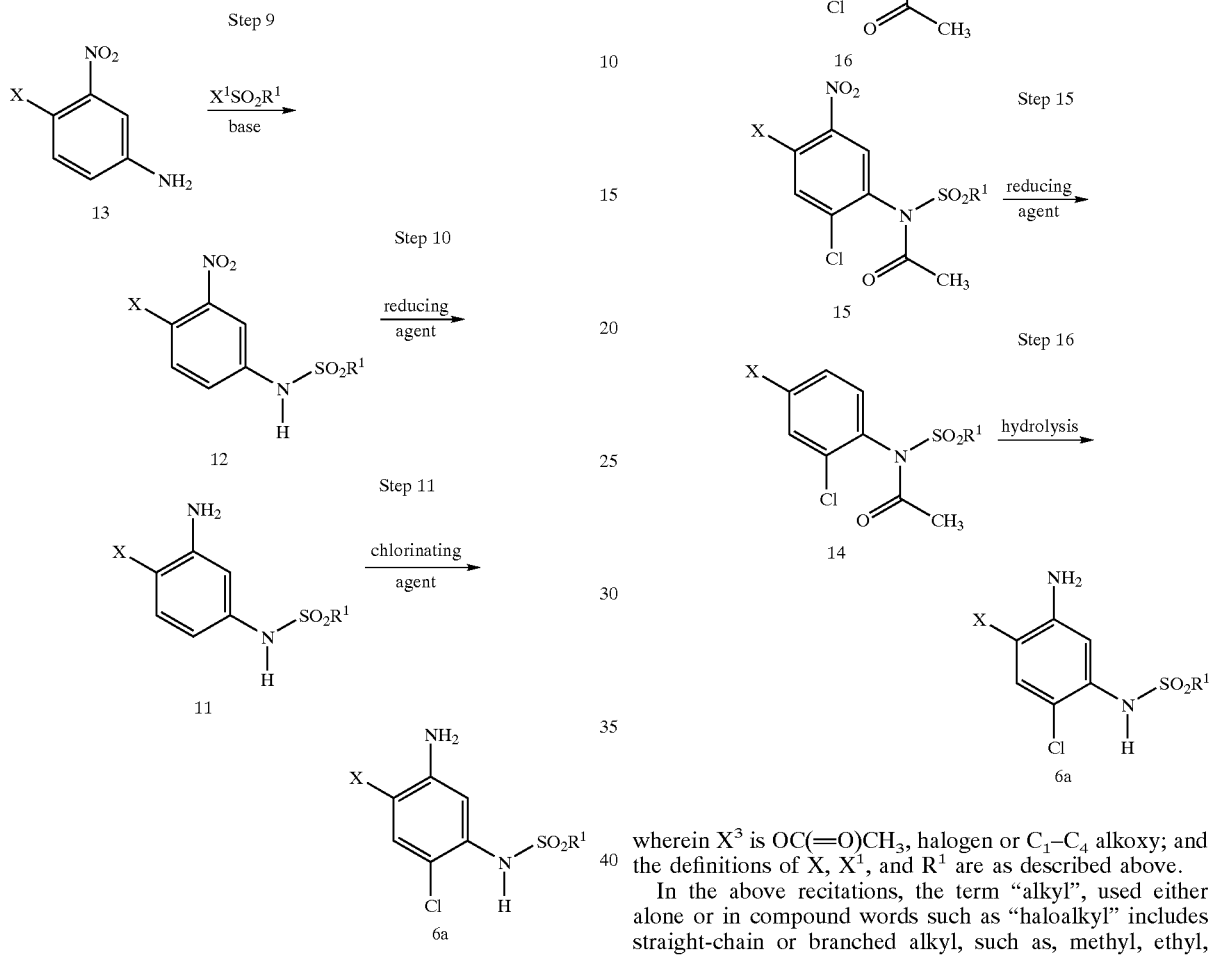

wherein the definitions of X, $X^1$, and $R^1$ are as described above.

Further processes of this invention to prepare intermediates of Formula 6a are illustrated below.

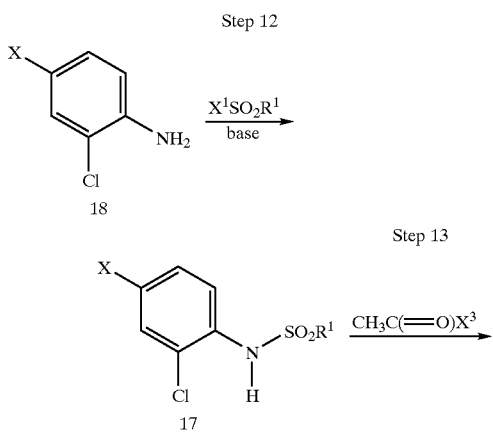

wherein $X^3$ is OC(=O)CH$_3$, halogen or $C_1$–$C_4$ alkoxy; and the definitions of X, $X^1$, and $R^1$ are as described above.

In the above recitations, the term "alkyl", used either alone or in compound words such as "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include CH$_3$OCH$_2$, CH$_3$OCH$_2$CH$_2$, CH$_3$CH$_2$OCH$_2$, CH$_3$CH$_2$CH$_2$CH$_2$OCH$_2$ and CH$_3$CH$_2$OCH$_2$CH$_2$. "Alkylthio" includes branched or straight-chain alkylthio moieties such as methylthio, ethylthio, and the different propylthio, butylthio, pentylthio and hexylthio isomers. "Cyanoalkyl" denotes an alkyl group substituted with one cyano group. Examples of "cyanoalkyl" include NCCH$_2$, NCCH$_2$CH$_2$ and CH$_3$CH(CN)CH$_2$.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkoxyalkyl", and the like, are defined analogously to the term "haloalkyl". Examples of "haloalkoxyalkyl" include $CF_3OCH_2$, $CCl_3CH_2OCH_2$, $HCF_2CH_2CH_2OCH_2$ and $CF_3CH_2OCH_2CH_2$.

The total number of carbon atoms in a substituent group is indicated by the "$C_i$–$C_j$" prefix where i and j are numbers from 1 to 6. For example, $C_1$–$C_3$ alkylsulfonyl designates methylsulfonyl through propylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$. Examples of "alkylcarbonyl" include $C(O)CH_3$, $C(O)CH_2CH_2CH_3$ and $C(O)CH(CH_3)_2$. Examples of "alkoxycarbonyl" include $CH_3OC(=O)$, $CH_3CH_2OC(=O)$, $CH_3CH_2CH_2OC(=O)$, $(CH_3)_2CHOC(=O)$ and the different butoxy- or pentoxycarbonyl isomers. Examples of "alkylcarbonyloxy" include $OC(O)CH_3$, $OC(O)CH_2CH_2CH_3$ and $OC(O)CH(CH_3)_2$.

When a compound is substituted with a substituent bearing a subscript that indicates the number of said substituents can exceed 1, said substituents (when they exceed 1) are independently selected from the group of defined substituents. Further, when the subscript indicates a range, e.g. $(R)_{i-j}$, then the number of substituents may be selected from the integers between i and j inclusive.

When a group contains a substituent which can be hydrogen, for example $R^2$, then, when this substituent is taken as hydrogen, it is recognized that this is equivalent to said group being unsubstituted.

Preferred intermediates of Formula 3 for reasons of better activity and/or ease of synthesis are those wherein $R^2$ is H and $R^1$ is $C_1$–$C_3$ haloalkyl. Most preferred are the intermediates wherein $R^1$ is $CH_2Cl$.

Preferred intermediates of Formula 6 for reasons of better activity and/or ease of synthesis are those wherein $R^2$ is H and $R^1$ is $C_1$–$C_3$ haloalkyl. Most preferred are the intermediates wherein $R^1$ is $CH_2Cl$.

A preferred process for the preparation of a compound of Formula 1 for reasons of better activity and/or ease of synthesis is the process of Step 8 wherein $R^2$ is H and $R^1$ is $C_1$–$C_3$ haloalkyl. Most preferred is the process of Step 8 wherein X is F, Y is Cl, and $R^1$ is $CH_2Cl$.

A preferred process for the preparation of a compound of Formula 2 for reasons of better activity and/or ease of synthesis is the process of Step 7 wherein $R^2$ is H and $R^1$ is $C_1$–$C_3$ haloalkyl. Most preferred is the process of Step 7 wherein X is F, Y is Cl, and $R^1$ is $CH_2Cl$.

A preferred process for the preparation of a compound of Formula 3 for reasons of better activity and/or ease of synthesis is the process of Step 6 wherein $R^2$ is H and $R^1$ is $C_1$–$C_3$ haloalkyl. Most preferred is the process of Step 6 wherein X is F, Y is Cl, and $R^1$ is $CH_2Cl$.

A preferred process for the preparation of a compound of Formula 6 for reasons of better activity and/or ease of synthesis is the process comprising of Steps 3 and 4 wherein $R^2$ is H, $R^1$ is $C_1$–$C_3$ haloalkyl, and $X^1$ is halogen. Most preferred is the process comprising of Steps 3 and 4 wherein X is F, Y is Cl, $R^1$ is $CH_2Cl$, and $X^1$ is Cl.

A preferred process for the preparation of a compound of Formula 6a for reasons of better activity and/or ease of synthesis is the process comprising of Steps 10 and 11 wherein $R^1$ is $C_1$–$C_3$ haloalkyl. Most preferred is the process comprising of Steps 10 and 11 wherein X is F and $R^1$ is $CH_2Cl$.

Another preferred process for the preparation of a compound of Formula 6a for reasons of better activity and/or ease of synthesis is the process comprising of Steps 15 and 16 wherein $R^1$ is $C_1$–$C_3$ haloalkyl. Most preferred is the process comprising of Steps 15 and 16 wherein X is F and $R^1$ is $CH_2Cl$.

A preferred process for the preparation of a compound of Formula 1 for reasons of better activity and/or ease of synthesis is the process comprising of Steps 7 and 8 wherein $R^3$ is OH, $R^2$ is H, and $R^1$ is $C_1$–$C_3$ haloalkyl. Most preferred is the process comprising of Steps 7 and 8 wherein X is F, Y is Cl, and $R^1$ is $CH_2Cl$.

A preferred process for the preparation of a compound of Formula 1 for reasons of better activity and/or ease of synthesis is the process comprising of Steps 6 and 7 wherein $R^2$ is H and $R^1$ is $C_1$–$C_3$ haloalkyl. Most preferred is the process comprising of Steps 6 and 7 wherein X is F, Y is Cl, and $R^1$ is $CH_2Cl$.

Step 1

Step 1 forms compounds of Formula 9 by reacting compounds of Formula 10 with a suitable nitrating agent.

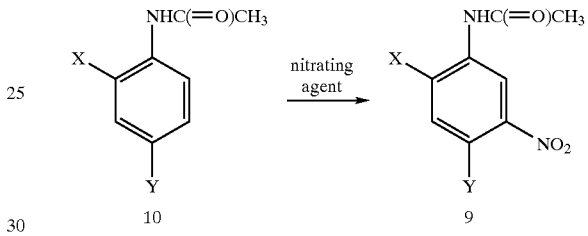

The reaction conditions for the nitration of Step 1 are well known in the art; see, for example, *Houben-Weyl, Methoden der Organischen Chemie,* Vol X/1 pp 479 and Vol. E 16 d, pp 262. Suitable nitrating agents include nitrogen (III) compounds (e.g., metal nitrites), nitrogen (V) compounds (e.g., metal nitrates, ammonium nitrates), nitronium compounds, nitric acid, fuming nitric acid, nitric acid in the presence of metal salts, nitric acid in the presence of inorganic acids, nitric acid in the presence of carboxylic acids such as glacial acetic acid or carboxylic acid anhydrides such as acetic anhydride, nitric acid in the presence of sulfonic acids, and nitric acid alkyl ethers. Additional nitrating reagents are described in the cited literature above. Preferred nitrating agents are fuming nitric acid or nitric acid in the presence of sulfuric acid. More preferred is the application of "nitrating acid" which is a mixture of nitric acid of different concentrations (68–100%) in the presence of concentrated sulfuric acid. Typical ratios range from 20% nitric acid:60% sulfuric acid:20% water up to 50% nitric acid:50% sulfuric acid. The most preferred ratio is equal amounts of fuming nitric acid and concentrated sulfuric acid. Nitrations may also be performed in inert solvents such as chlorocarbons, hydrocarbons, ethers or alcohols. Concentrated sulfuric acid or a mixture of concentrated sulfuric acid and oleum are preferred as solvents; most preferred is a mixture of concentrated sulfuric acid and oleum. Oleum containing between 20% and 65% sulfur trioxide can be applied. The optimum amount of oleum is that amount which traps the water which is generated during the reaction; thus, equimolar amounts of oleum and nitric acid are most preferred.

The nitrations can be performed at temperatures between −50 and 100° C. Preferred temperatures are between −20 and 30° C., with the most preferred reaction temperatures at −5 to 5° C.

Step 2

Step 2 forms compounds of Formula 8 by reacting compounds of Formula 9 with hydrogen in the presence of a hydrogenation catalyst or by reaction with other reducing agents.

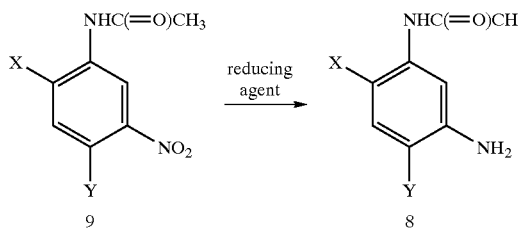

The reduction of compounds of Formula 9 in Step 2 can be achieved under well known hydrogenation conditions with metal catalysts such as Pt, Pd, Re, Rh, Ru, Ir, Ni, optionally with the use of promoters or accelerators. Non-catalytic reductions can be achieved, for example, with molar amounts of iron, iron salts, tin, tin salts, low valent sulfur compounds, lithium aluminum hydride, hydrazines, and other reducing agents as described in *Houben-Weyl, Methoden der Organischen Chemie,* Vol. II/1, p 360 and Vol. IV/2, p 506.

The catalytic hydrogenation can be performed in inert solvents such as alcohols, ethers, esters, ketones, amides or pyridine at temperatures between 0 and 160° C. at atmospheric or elevated pressure between 100 and 10,000 kPa (1 and 100 atmospheres) in substrate:solvent dilutions between 1:1 and 1:100. Reducing agents such as hydrazines, unsaturated hydrocarbons such as cyclohexene or formic acid can be used in place of molecular hydrogen.

Preferably, the reaction is run with molecular hydrogen in the presence of an iridium catalyst in ethyl acetate at 100 to 10,000 kPa (1 to 100 atmospheres) pressure at temperatures between 30 and 120° C. at concentrations of 0.01 to 5 M. More preferred is hydrogenation with molecular hydrogen at 200 to 6,000 kPa (2 to 60 atmospheres) of pressure, a temperature of 65–90° C. and concentrations of 0.2–1.0 M.

The reduction can also be achieved by the Bechamp method and variations thereof as described in *Houben-Weyl, Methoden der Organischen Chemie,* Vol II/1, p 394. The reaction can be run under neutral or acidic conditions in inert solvents such as esters, alcohols, aqueous alcohols, water, glacial acetic acid or hydrocarbons. Mineral acids (e.g., hydrochloric acid) or organic acids (e.g., acetic acid) can be used as acidic activators. The temperature may vary between 0° C. and the boiling point of the solvent.

Preferred is the reduction in ethanol at temperatures between 30° C. and the boiling point of the solvent with acetic acid as activator. The preferred molar ratio of substrate:acid:iron is 1:2–4:6–10.

The product can be isolated as a solid by removal of the catalyst by filtration and removal of the solvent by distillation. The solution can also be used directly in the next reaction. Preferably, the filtered solution is partially concentrated to a slurry and used directly in the next reaction.

Step 3

Step 3 forms compounds of Formula 7 (wherein $R^2$ is H) by reacting compounds of Formula 8 with a sulfonyl halide of formula $X^1SO_2R^1$ in the presence of a base. Optionally, compounds of Formula 7 (wherein $R^2$ is other than H) are formed by reacting compounds of Formula 7 (wherein $R^2$ is H) with compounds of $R^2X^1$ in the presence of a suitable base such as triethylamine, pyridine or N,N-dimethylaniline and optionally a suitable solvent such as a hydrocarbon, a halogenated hydrocarbon or an aromatic hydrocarbon.

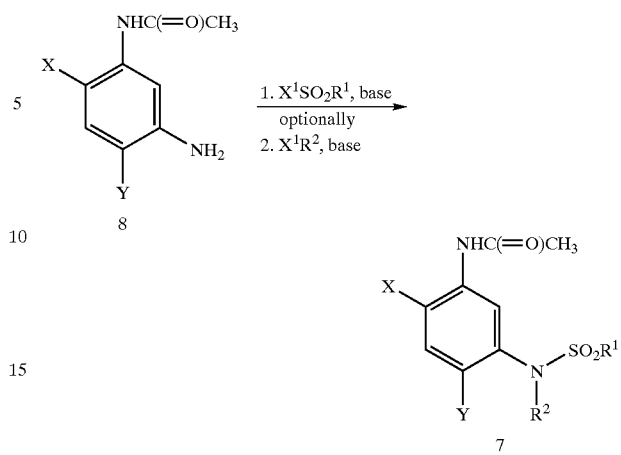

The sulfonamidation can be performed under well known conditions as described in *Houben-Weyl, Methoden der Organischen Chemie,* Vol IX, pp 609–614.

Preferably, the solution from Step 2 is concentrated to a slurry and used directly in the reaction of Step 3 by adding 1–100 molar equivalents of an organic or inorganic base, (preferred bases are organic bases such as pyridine, alkylpyridines or dialkylaminopyridines; most preferred is pyridine) and chloromethanesulfonyl chloride at −10 to 70° C. Most preferred is the reaction of Step 3 wherein 7–13 equivalents of pyridine are added and the reaction temperature is initially in the range of 0 to 40° C. and is later raised to 80 to 130° C. The reaction proceeds in inert solvents such as esters, acetates, ketones, chlorocarbons, nitrites and pyridine. Preferred are ethyl acetate, pyridine or mixtures thereof; most preferred is pyridine. Alternatively, the reaction can be run at temperatures between 20 and 300° C. without a base by heating the components in a solvent such as an ester, ketone, chlorocarbon or hydrocarbon or with a base under phase transfer conditions between 0 and 100° C. as described in the literature (see, for example, C. M. Starks, C. L. Liotta, M. Halpern, *Phase Transfer Catalysis,* Chapman and Hall (1994) or DE patent 2,941,593), preferably with a ketone or chlorocarbon solvent. Most preferred solvents are methyl isobutyl ketone, dichloroethane, chloroform or methylene chloride.

Step 4

Step 4 forms compounds of Formula 6 by hydrolyzing the compounds of Formula 7 with acid or base.

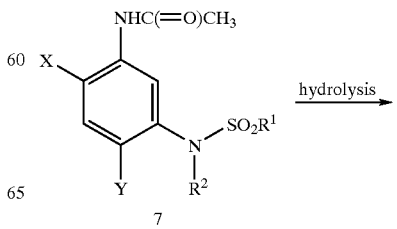

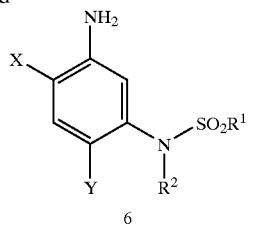

The crude reaction product of Formula 7 can be isolated by filtration; however, preferably the crude reaction product of Formula 7 is used directly without isolation in Step 4 by hydrolysis under basic or acidic conditions with mineral acids or inorganic bases at temperature between 30–120° C. and a pressure of 100 kPa (1 atmosphere) or greater. Most preferred basic conditions include reaction temperatures of 50–55° C. and 6 N NaOH. Most preferred acidic conditions include reaction temperatures of 90–110° C. and 6 N HCl. Acidic hydrolysis is more preferred than basic methods of hydrolysis.

The product of Formula 6 can be recrystallized from organic solvents such as esters, ketones, aromatic hydrocarbons and chlorocarbons. Preferred is recrystallization from methyl isobutyl ketone, toluene or mixtures thereof.

Step 5

Step 5 forms compounds of Formula 5 by reacting compounds of Formula 6 with a phosgenating agent.

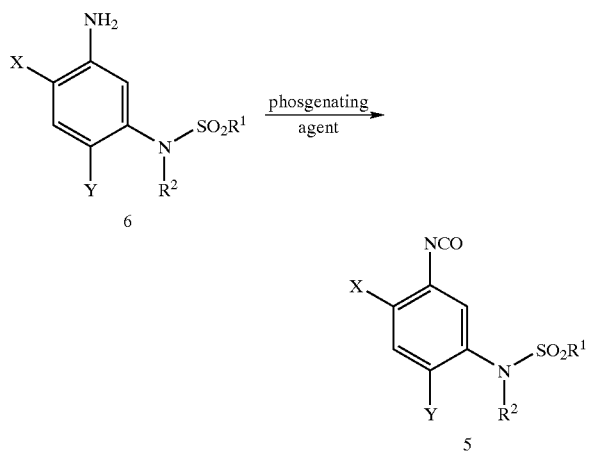

The phosgenation of Step 5 can be performed by methods well known in the art (see, for example, *Houben-Weyl, Methoden der Organischen Chemie,* Vol. E 4) in aprotic organic solvents such as aliphatic hydrocarbons, aromatic hydrocarbons, aliphatic and aromatic chlorocarbons, chloroolefins, esters, ethers, ketones, nitrites, sulfones and nitroarenes at temperatures between −50 and 150° C. with about 1 to 50 equivalents of a phosgenating agent such as phosgene, diphosgene, triphosgene, carbonyldiimidazole or carbamates from which the isocyanate is generated by elimination of alcohol. The phosgenation is preferably performed in a ketone or ether solvent, most preferably in methyl isobutyl ketone, or dimethoxyethane at temperatures between −50 and 150° C., preferably between −10 and 80° C., most preferably between 0 and 50° C., with preferably about 1 to 10 equivalents of phosgene, and most preferably with 1.0 to 1.5 equivalents of phosgene.

Alternatively, the aniline of Formula 6 can be reacted with an alkali cyanate to give a urea intermediate which can be used for the following coupling Step 6.

Alternatively, the aniline of Formula 6 after the hydrolysis reaction of Step 4 can after neutralization be extracted directly into a suitable organic solvent, preferably a ketone or toluene, most preferably methyl isobutyl ketone, at room temperature or at an elevated temperature and used in the phosgenation of Step 5. By this means, water can be removed from the solution of a compound of Formula 6 by azeotropic distillation.

Step 6

Step 6 forms compounds of Formula 3 by reacting compounds of Formula 5 with compounds of Formula 4.

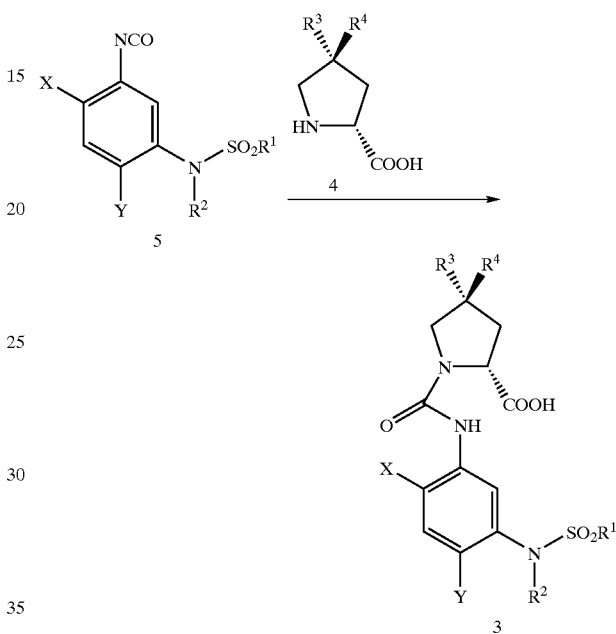

Step 6 can be conducted in a single liquid phase which is a suitable solvent or it can be carried out in a two-phase system consisting of an aqueous phase and a suitable organic solvent. In the single phase coupling process, the compound of Formula 4 is suspended at 0–120° C. in an organic solution consisting of an isocyanate of Formula 5 in a solvent such as a hydrocarbon, chlorocarbon, ether, ester, ketone, and preferably chlorobenzene, dichlorobenzene, dimethoxyethane, tetrahydorfuran or methyl isobutyl ketone.

Preferred solvents for the single phase process step are those toward which the isocyanate of Formula 5 is unreactive and which dissolve the compound of Formula 4 to the extent necessary for the reaction to proceed, and include ethers such as dimethoxyethane and tetrahydrofuran, esters such as ethyl acetate, or ketones such as acetone. Preferred reaction conditions include a temperature from about 0 to 100° C., and a reaction time from about 30 minutes to 48 hours. More preferred are temperatures from about 20 to 40° C. and reaction times from 2 hours to 24 hours. Particularly preferred for achieving high yields of compounds of Formula 3 is the process wherein the solvent is tetrahydrofuran. Also preferred for this process is the use of an excess of the compound of Formula 4, which excess can be removed by filtration once the reaction is complete, providing a solution of the product of Formula 3. Optionally, this product can be further purified by extraction into aqueous alkali, acidification of the aqueous solution, and isolation of the product of Formula 3 by filtration or by extraction into a suitable organic solvent.

More preferred is a two-phase system wherein the organic solution of the isocyanate of Formula 5 is added to the compound of Formula 4 or a suitable salt thereof dissolved in aqueous base, preferably sodium hydroxide. The aqueous phase has a concentration between 0.1 and 10 M and contains 1 to 10 equivalents of the compound of Formula 4 with 1 to 10 equivalents of base with respect to the compound of Formula 4. It is preferred to run the reaction at concentrations between 0.5 and 5 M, and most preferred between 1 and 3 M. 1–5 equivalents of the compound of Formula 4 are preferred; most preferred is 1 to 1.5 equivalents. Solvents such as ketones, chlorobenzene, dichlorobenzene and dimethoxyethane and mixtures thereof are preferred, with ketones such as methyl isobutyl ketone being most preferred. The coupling reaction is done at temperatures between −15 and 100° C., preferably between −10 and 40° C.

Suitable organic solvents for the two-phase process include halocarbons such as chloroform or dichloromethane, esters such as ethyl acetate, or ketones such as methyl isobutyl ketone. The aqueous phase is a solution of the compound of Formula 4 or a suitable salt thereof and a base, preferably sodium hydroxide. The two phases are contacted at a temperature of about −10 to about 50° C., preferably at about 0° C. After completion of the reaction and separation of the aqueous phase, the aqueous phase is acidified with mineral acid and the product of Formula 3 can be isolated by filtration or extracted into a suitable organic solvent.

In the two-phase coupling step the pH is adjusted to between 7.5 and 4.5, preferably to about pH 6–7 and the organic layer removed. The aqueous solution of Step 6 is further acidified to about pH 0 to 4, preferably about pH 2, and extracted with an organic solvent such as a hydrocarbon, chlorocarbon, ester, or ketone, preferably with the same solvent as used in the preceding Step 5, most preferably methyl isobutyl ketone.

The product can be isolated from the organic phase by distilling off the solvent or by precipitation. Alternatively, the organic phase can be optionally dried with a suitable material such as sodium sulfate or magnesium sulfate or by azeotropic distillation. Most preferred is to use the product of Step 6 directly in the next reaction Step 7.

Compounds of Formula 4 wherein $R^3$ is H and $R^4$ is F or Cl, i.e., trans-4-fluoro-D-proline or trans-4-chloro-D-proline, can be made from the compound of Formula 4 wherein $R^3$ is OH and $R^4$ is H, cis-4-hydroxy-D-proline, by first protecting the carboxylic acid and amino functions with suitable protecting groups or other derivatives, followed by reacting this protected compound with a halogenating agent such as those described in the references listed within, optionally after converting the hydroxyl function to a leaving group, and finally removing the protecting groups. Appropriate choices of protecting groups or other derivatives and leaving groups and methods for their application will be apparent to one skilled in the art. Syntheses of the enantiomeric compounds trans-4-fluoro-L-proline and trans4-chloro-L-proline are described in *Biochemistry* (1965) 4, 2507 and in *Aust. J. Chem.* (1967) 20, 1493, respectively.

Step 7

Step 7 forms compounds of Formula 2 by reacting compounds of Formula 3 with a cyclizing agent.

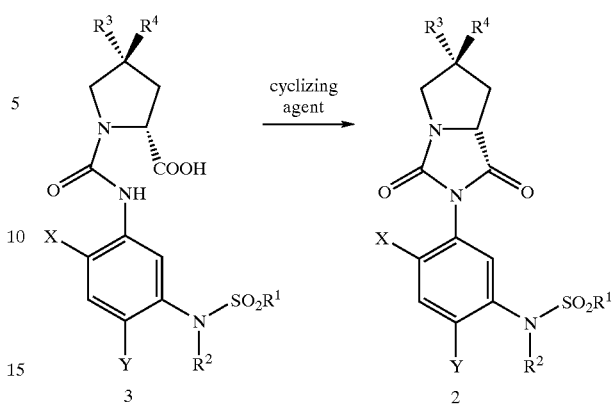

The cyclizing agent of Step 7 can be an acid or any suitable reagent for cyclizing the activated form of compounds of Formula 3. Suitable reagents for cyclizing thus include alkylchloroformates in the presence of an acid or a base, carbodiimides or anhydrides. The cyclization of the compounds of Formula 3 can proceed in organic solvents such as chlorocarbons, esters, ethers, ketones or nitriles. The cyclization can also be induced by allowing the solution of compound of Formula 3 to stand at room temperature or, preferably, thermally by heating the compound of Formula 3 in a solvent such as methyl isobutyl ketone at 100 kPa (1 atmosphere) or elevated pressure. Preferred cyclization conditions are the addition of 0.01–10 equivalents of a strong acid such as hydrochloric acid, phosphoric acid, acetic acid, trifluoroacetic acid or a strong "solid acid", or cyclization with dicyclohexyl carbodiimide in the presence of N-hydroxysuccinimide.

The most preferred cyclization conditions include 0.5–2 equivalents of concentrated sulfuric acid in methyl isobutyl ketone at 0–120° C. Thus, the product of the previous Step 6 as an aqueous solution of the compound of Formula 3 at pH 6 is further acidified to pH 2–3 and extracted into an organic solvent, most preferred methyl isobutyl ketone. From this solution water can optionally be removed by azeotropic distillation. The compound of Formula 3 is then cyclized to the compound of Formula 2 by the addition of 0.01–10 equivalents of a strong acid such as hydrochloric acid, phosphoric acid, acetic acid, or trifluoroacetic acid, most preferably 0.5–1 equivalent of concentrated sulfuric acid, at 0–120° C., most preferably in refluxing methyl isobutyl ketone.

In addition to the reagents and reaction conditions detailed above, compounds of Formula 3 wherein $R^4$ is F or Cl can also be cyclized to compounds of Formula 2 wherein $R^4$ is F or Cl by converting the carboxylic acid function of the compound of Formula 3 to an activated form by a further number of methods known to the skilled artisan. These activated forms include (a) acid halides, obtained by treatment of compounds of Formula 3 with thionyl chloride, oxalyl chloride or equivalent reagents; (b) mixed anhydrides, obtained by treatment of compounds of Formula 3 with phosgene, alkyl chloroformates, phosphoryl chlorides, acetic anhydride or equivalent reagents; and (c) activated esters, obtained by treatment of compounds of Formula 3 with dicyclohexylcarbodiimide and N-hydroxysuccinimide or equivalent reagents. The preferred process is reaction of a compound of Formula 3 with thionyl chloride in a suitable solvent at a temperature of about 0 to 100° C., with a reaction time of about 30 minutes to 48 hours. Suitable solvents for this preferred process include halocarbons such as chloroform, dichloromethane or dichloroethane, ethers such as tetrahydrofuran or dimethoxyethane, esters such as ethyl acetate, ketones such as acetone or methyl isobutyl ketone, or other aprotic solvents such as acetonitrile. Also preferred is the use of a catalyst such as pyridine or N,N-dimethylformamide. Most preferred is the process with dichloromethane as solvent, at a temperature of about 20 to 40° C., with a reaction time of about 2 to 24 hours. The product of Formula 2 can be isolated from the reaction mixture by evaporating the volatiles, replacing the dichloromethane with a solvent in which the product has less solubility, and filtration. Alternatively, the crude product can be converted to a salt by treatment with, e.g., an amine compound. After isolating this salt, the product of Formula 2 can be liberated by treating the salt with a mineral acid.

Step 8

Step 8 forms compounds of Formula 1 by reacting compounds of Formula 2a with a halogenating agent in a suitable solvent.

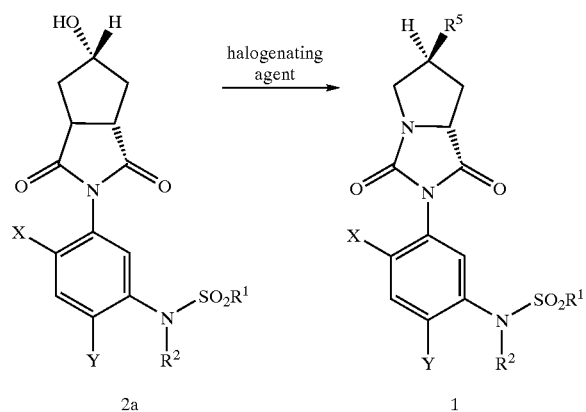

The halogenating agent is a chlorinating agent such as thionyl chloride or phosphorous pentachloride, or a fluorinating agent such as diethylaminosulfur trifluoride, sulfur tetrafluoride or a fluorinated amine reagent. Other fluorinating agents include those described in *Tetrahedron* (1993) 49, 9385; *Aldrichimica Acta* (1993) 26, 47; *Tetrahedron Letters* (1989) 30, 3077; *Tetrahedron Letters* (1995) 36, 2611; and *Tetrahedron* (1996) 52, 2977. For the process of Step 8, the temperature is from about 0 to 200° C., the pressure is from about 100 to about 500 kPa (1 to about 5 atmospheres) and the reaction time is from about 1 minute to 24 hours. Suitable solvents include halocarbons such as chloroform, dichloromethane, dichloroethane, fluorobenzene, benzotrifluoride, chlorobenzene, or dichlorobenzene; hydrocarbons such as benzene, toluene, or xylene and fluoro-derivatives thereof; ethers such as diphenyl ether, dioxane or dimethoxyethane; esters such as n-propyl acetate or isobutyl acetate; ketones such as methyl isobutyl ketone, 4-heptanone or cyclohexanone; or nitriles such as acetonitrile or benzonitrile. The molar ratio of the compound of Formula 2a to the halogenating agent is typically from about 1:1 to 1:5.

Preferred are processes wherein the halogenating agent is a fluorinated amine reagent of formula $R^6R^7NCF_2CFHR^8$, the temperature is from about 30 to 180° C., and the molar ratio of the compound of Formula 2a to halogenating agent is from about 1:1 to 1:2. $R^6$ and $R^7$ are independently $C_1$–$C_{10}$alkyl or branched alkyl groups such as methyl, ethyl or isopropyl, or they may be taken together to form a ring such as —CH$_2$(CH$_2$)$_3$CH$_2$— or —CH$_2$(CH$_2$)$_4$CH$_2$—; $R^8$ is a halogen such as chlorine or fluorine, or $R^8$ is a $C_1$–$C_4$ haloalkyl group such as trifluoromethyl. These fluorinated amine reagents may be prepared by methods described in *Bull. Chem. Soc. Japan* (1979) 52, 3377 or modifications thereof. Other methods of preparation include the reaction of an olefin with a dialkylamine, for example the reaction of hexafluoropropene with diethylamine, or the reaction of a fluoro-olefin such as chlorotrifluoroethylene, tetrafluoroethylene or other polyfluorinated olefin with an alkylamine, dialkylamine, or cyclic amine.

Most preferred are processes wherein the halogenating agent is a fluorinated amine reagent of formula $R^6R^7NCF_2CFHR^8$, where $R^6$ and $R^7$ are each independently methyl or ethyl, and $R^8$ is fluoro or trifluoromethyl. Most preferred reaction conditions include a temperature of about 40 to 120° C., a pressure of about 100 to about 200 kPa (1 to 2 atmospheres), and a reaction time of about 1 minute to 4 hours in a solvent which is dichloromethane, chloroform, chlorobenzene, fluorobenzene, toluene or isopropyl acetate. The molar ratio of the compound of Formula 2a to the halogenating agent is from about 1:1.0 to 1:1.2, and the reaction vessel is constructed of a material which is substantially unreactive with the fluorinating agent and hydrogen fluoride under the reaction conditions.

The product of Formula 1 can be isolated from the reaction mixture in various ways. In some cases, the compound of Formula 1 can be crystallized from the reaction mixture, and can be isolated by filtration, optionally after removal of volatile by-products and some portion of the reaction solvent by distillation and/or extraction with water. It can also be advantageous to crystallize the compound of Formula 1 from a suitable solvent, optionally with removal of some or all volatile by-products and reaction solvent by distillation and/or extraction with water. Suitable solvents for crystallization of the compound of Formula 1 include, but are not limited to, alcohols such as methanol, ethanol, n-propanol, i-propanol, i-butanol, amyl alcohol, cyclohexanol or 1-heptanol; ketones such as methyl isobutyl ketone or cyclohexanone; ethers such as diphenyl ether or methyl tert-butyl ether; halocarbons such as dichloroethane, trichloroethane, chlorobenzene, dichlorobenzene, fluorobenzene or benzotrifluoride; and hydrocarbons such as toluene or xylene, including mixtures and aqueous mixtures thereof. Alternatively, it is sometimes more convenient to convert the compound of Formula 1 to a salt by treatment with, for example, an amine compound, and to first isolate this salt by filtration. The product of Formula 1 can then be liberated by treating this salt with a mineral acid.

Step 9

Step 9 forms compounds of Formula 12 by reacting compounds of Formula 13 with a sulfonyl halide of formula $X^1SO_2R^1$ in the presence of a base.

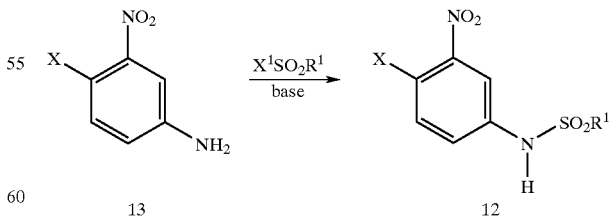

The sulfonamidation can be performed under well known conditions as described in *Houben-Weyl, Methoden der Organischen Chemie,* Vol IX, pp 609–614.

Preferably, the reaction of Step 9 employs 1–100 molar equivalents of an organic or inorganic base, (preferred bases are organic bases such as pyridine, alkylpyridines or dialkylaminopyridines; most preferred is pyridine) and chloromethanesulfonyl chloride at −10 to 70° C. The reaction proceeds in inert solvents such as esters, acetates, ketones, chlorocarbons, nitriles and pyridine. Preferred solvents are ethyl acetate, pyridine or mixtures thereof; most preferred is pyridine. Alternatively, the reaction can be run at temperatures between 20 and 300° C. without a base by heating the components in a solvent such as an ester, ketone, chlorocarbon or hydrocarbon or with a base under phase transfer conditions between 0 and 100° C. as described in the literature (see, for example, C. M. Starks, C. L. Liotta, M. Halpern, *Phase Transfer Catalysis*, Chapman and Hall (1994), or DE patent 2,941,593), preferably with a ketone or chlorocarbon solvent. Most preferred solvents are methyl isobutyl ketone, dichloroethane, chloroform or methylene chloride.

Step 10

Step 10 forms compounds of Formula 11 by reacting compounds of Formula 12 with hydrogen in the presence of a hydrogenation catalyst or by reaction with other reducing agents.

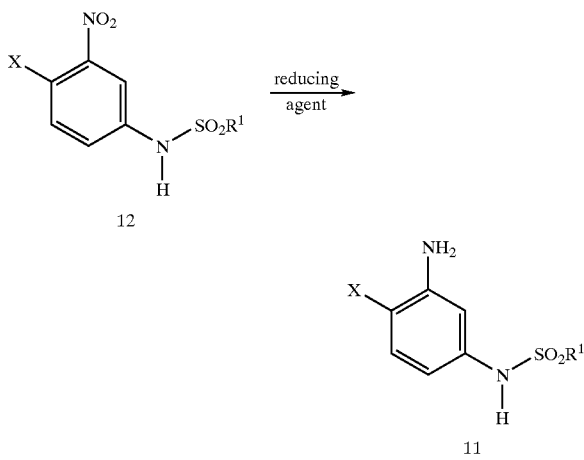

The reduction of compounds of Formula 12 in Step 10 can be achieved under well known hydrogenation conditions with metal catalysts such as Pt or Pd, optionally with the use of promoters or accelerators. Non-catalytic reductions can be achieved, for example, with molar amounts of iron, iron salts, tin, tin salts, low valent sulfur compounds, lithium aluminum hydride, hydrazines, and other reducing agents as described in *Houben-Weyl, Methoden der Organischen Chemie*, Vol. II/1, p 360 and Vol. IV/2, p 506.

The catalytic hydrogenation can be performed in inert solvents such as alcohols, ethers, esters, ketones, amides or pyridine at temperatures between 0 and 160° C. and at a pressure between 100 and 10,000 kPa (1 and 100 atmospheres) in substrate:solvent dilutions between 1:1 and 1:100. Reducing agents such as hydrazines, unsaturated hydrocarbons such as cyclohexene or formic acid can be used in place of molecular hydrogen.

The reduction can also be achieved by the Bechamp method and variations thereof as described in *Houben-Weyl, Methoden der Organischen Chemie*, Vol II/1, p 394. The reaction can be run under neutral or acidic conditions in inert solvents such as esters, alcohols, aqueous alcohols, water, glacial acetic acid or hydrocarbons. Mineral acids (e.g., hydrochloric acid) or organic acids (e.g., acetic acid) can be used as acidic activators. The temperature may vary between 0° C. and the boiling point of the solvent.

Preferred is the reduction in ethanol at temperatures between 30° C. and the boiling point of the solvent with acetic acid as activator. The preferred molar ratio of substrate:acid:iron is 1:2–4:6–10.

The product can be isolated as a solid by removal of the catalyst by filtration and removal of the solvent by distillation.

Step 11

Step 11 forms compounds of Formula 6a by reacting compounds of Formula 11 with a chlorinating agent.

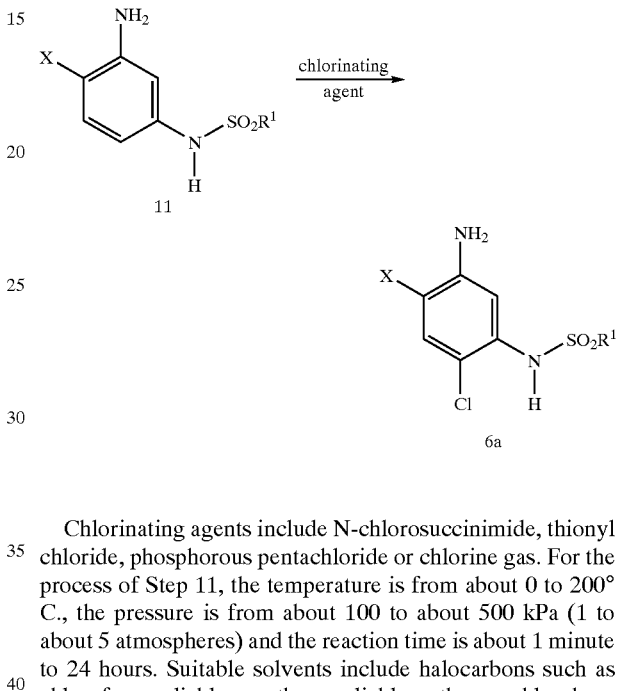

Chlorinating agents include N-chlorosuccinimide, thionyl chloride, phosphorous pentachloride or chlorine gas. For the process of Step 11, the temperature is from about 0 to 200° C., the pressure is from about 100 to about 500 kPa (1 to about 5 atmospheres) and the reaction time is about 1 minute to 24 hours. Suitable solvents include halocarbons such as chloroform, dichloromethane, dichloroethane, chlorobenzene or dichlorobenzene, hydrocarbons such as benzene, toluene or xylene, and other solvents such as dimethylformamide. The molar ratio of the compound of Formula 11 to the halogenating agent is typically from 1:1 to 1:1.2.

The preferred chlorinating reaction conditions are N-chlorosuccinimide in dimethylformamide at a temperature of 50° C. The molar ratio of the compound of Formula 11 to N-chlorosuccinimide is 1:1.1.

The product can be isolated by diluting the reaction with ethyl acetate and washing with water. Separation of the organic layer and removal of the solvent by distillation provides a product which can be purified by crystallization using appropriate solvents such as a chlorobutane/ether mixture, or by flash chromatography eluting with an appropriate hydrocarbon solvent mixture such as hexane and ethyl acetate.

Step 12

Step 12 forms compounds of Formula 17 by reacting compounds of Formula 18 with a sulfonyl halide of formula $X^1 SO_2R^1$ in the presence of a base. The sulfonamidation can be done under conditions well known in the art; see, for example, Houben-Weyl, *Methoden der Organischen Chemie, Vol. IX*, pp 609–614.

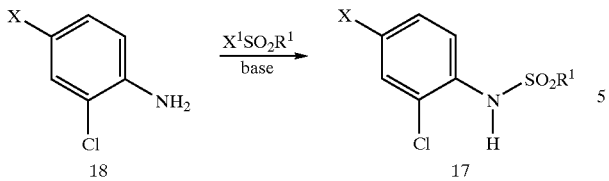

Compounds of Formula 18 can be reacted with a sulfonyl halide of formula $X^1SO_2R^1$ in a variety of inert organic solvents such as aliphatic and aromatic hydrocarbons, heteroarenes, halocarbons, esters, ketones and nitrites in the presence of organic bases such as mono-, di- and tri-alkylamines or, preferably, aromatic amines such as pyridines, alkylpyridines and dialkylpyridines, or inorganic bases such as sodium or potassium bicarbonate, sodium, potassium, lithium and magnesium carbonate. When an organic base is used, the reaction can also be run under conditions where the base serves as the solvent.

The preferred procedure consists of running the reaction of Step 2 in toluene or acetone, at temperatures between –30 and 50° C., most preferably at 5 to 10° C. The sulfonyl chloride is added to the solution such that the temperature does not exceed 10 to 15° C. After the addition is complete, the mixture is stirred an additional 30 minutes followed by the addition of 0.5 to 4 equivalents of an organic base, preferably 2 equivalents of triethylamine, at 5 to 10° C.

Step, 13

Step 13 forms compounds of Formula 16 by reacting compounds of Formula 17 with an acetylating agent of formula $CH_3C(=O)X^3$, wherein $X^3$ is $OC(=O)CH_3$, halogen or $C_{1-4}$ alkoxy.

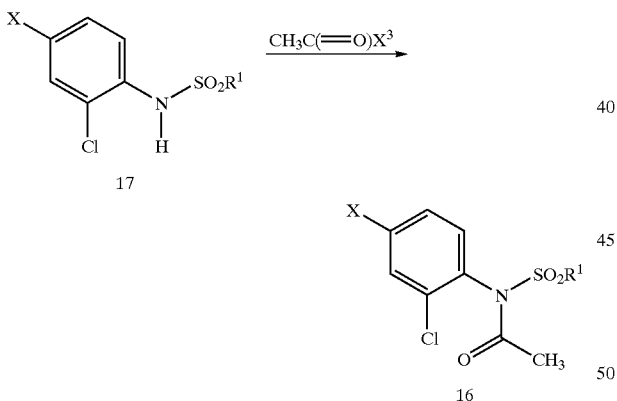

The compound of the Formula 17 can be acetylated under conditions well known in the art using a suitable carboxylic acid or a carboxylic acid derivative such as an anhydride, acyl halide or ester, optionally in the presence of a base. The preferred reaction conditions include reaction of the compound of Formula 17 with acetic anhydride at temperatures between –40 and 140° C. in a suitable inert solvent. Most preferably, the compound of Formula 17 is treated with acetic anhydride at a temperature of between 20° C. and reflux; the acetic anhydride serves as a solvent and as the acylating agent simultaneously.

Step 14

Step 14 forms compounds of Formula 15 by reacting compounds of Formula 16 with a nitrating agent.

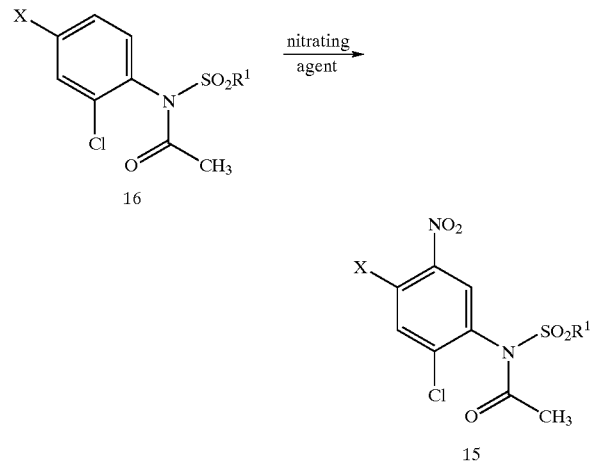

The reaction conditions for the nitration of Step 14 are well known in the art; see, for example, Houben-Weyl, *Methoden der Organischen Chemie*, Vol. X/1 p 479, and Vol. E 16d, p 262. The reaction conditions are as previously described for the nitration of the compound of Formula 10 in Step 1. Preferred reaction conditions are performing the reaction at 0–15° C. with 30% $SO_3$ dissolved in concentrated sulfuric acid in combination with a "nitrating acid" made from equal amounts of concentrated sulfuric acid and fuming nitric acid.

Step 15

Step 15 forms compounds of Formula 14 by reacting compounds of Formula 15 with a reducing agent.

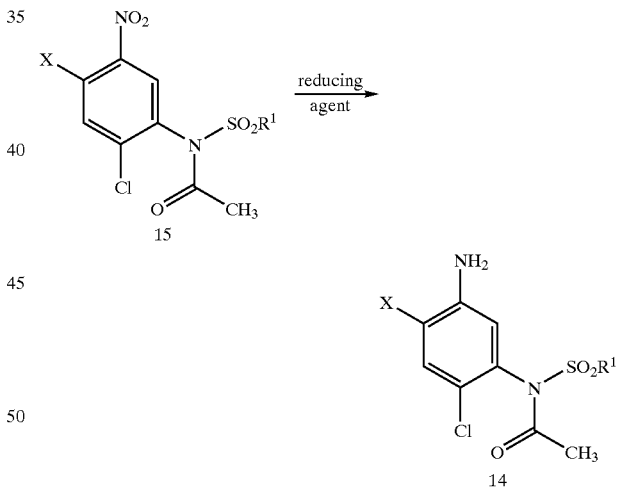

The compound of Formula 15 can be reduced to the compound of Formula 14 with reducing agents such as described in Houben-Weyl, *Methoden der Organischen Chemie*, Vol. II/1 p 360; also, see the reduction conditions described in Step 2. Alternatively, and preferably, the reduction is done in the presence of a metal catalyst by molecular hydrogen or hydrogen equivalents as described in Houben-Weyl, *Methoden der Organischen Chemie*, Vol. IV/2, p 506; also, see the reduction conditions described in Step 2. In the most preferred procedure, an iridium catalyst on carbon or a nickel catalyst is applied in ethanol at temperatures between 0 and 150° C. under a hydrogen pressure of 100 to 10,000 kPa (1 to 100 atmospheres).

Step 16

Step 16 forms compounds of Formula 6a by the hydrolysis of compounds of Formula 14.

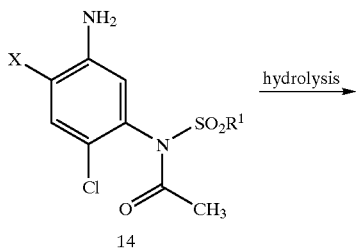

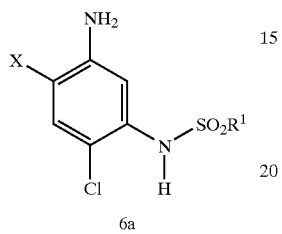

The conversion of a compound of Formula 14 to a compound of Formula 6a can be done under acidic or basic conditions in inert solvents in which the compound of Formula 14 is sufficiently soluble, at temperatures between 0° C. and the refluxing solvent. It is preferred to dissolve the starting material in a suitable alcohol, preferably ethanol, and to add aqueous sodium hydroxide as a base. The hydrolysis can then be done between room temperature and the refluxing solution, most preferably at 45–55° C.

It is recognized that some reagents and reaction conditions described above for preparing compounds of Formulae 1–17 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York (1991).

One skilled in the art will recognize that, in some cases, after the introduction of a given reagent as it is depicted in any individual scheme, it may be necessary to perform additional routine synthetic steps not described in detail to complete the synthesis of compounds of Formulae 1–17.

One skilled in the art will also recognize that it may be necessary to perform a combination of the steps illustrated in the above schemes in an order other than that implied by the particular sequence presented to prepare the compounds of Formulae 1–17.

One skilled in the art will also recognize that compounds of Formulae 1–17 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; s=singlet, d=doublet, t=triplet, q=quartet, m=multiplet, dd=doublet of doublets, dt=doublet of triplets, br s=broad singlet. HPLC is high pressure liquid chromatography. HPLC purity is area percentage.

Structures 3a and 1a are shown below to illustrate the Chemical Abstracts system of atom numbering and stereochemical designations used in the following examples.

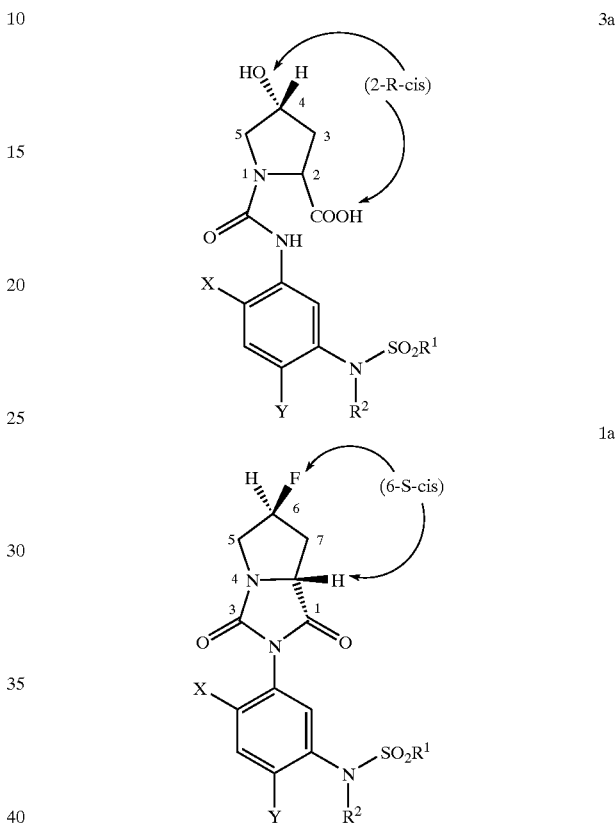

EXAMPLE 1

Preparation of N-(4-chloro-2-fluoro-5-nitrophenyl)acetamide

To a stirred solution of 375.2 g (2 mole) of N-(4-chloro-2-fluorophenyl)acetamide in 600 mL of concentrated sulfuric acid and 400 mL of oleum (30%) was added 166 mL of a 1:1 mixture of nitric acid (100%) and concentrated sulfuric acid at 0° C. over a period of 1.5 hours. After the addition was complete, the reaction mixture was poured into 11 L of ice water. The precipitate was filtered and the filter cake suspended in 200 mL of water. The solid was redissolved by the addition of 2 L of ethyl acetate and neutralized with aqueous NaOH to pH 7. The two phase mixture was heated to 50° C. and separated. The organic layer was washed with 150 mL of water. 200 mL of ethyl acetate were distilled off and the remaining solution was treated with 12 g of Celite® at 70° C., filtered and washed with another 200 mL of ethyl acetate.

The filtrate was concentrated to 1080 g and allowed to crystallize at 5° C. overnight. After filtration and drying, 384 g of the title compound was isolated as a solid melting at 145–149° C. (purity: >99.5% by HPLC). A second crystallization from the mother liquor afforded another 45.5 g of the title compound.

EXAMPLE 2

Preparation of N-(5-amino-4-chloro-2-fluorophenyl) acetamide

In a 20 L autoclave, 1395 g (6 mole) of N-(4-chloro-2-fluoro-5-nitrophenyl)acetamide and 14 g of Ir-catalyst (5% on carbon, 1% w/w) were suspended in 14 L of ethyl acetate. The autoclave was purged two times with nitrogen at 500 kPa (5 atmospheres) pressure followed by purging with hydrogen at 500 kPa (5 atmospheres). 400 kPa (4 atmospheres) pressure of hydrogen was applied for the hydrogenation and the mixture was heated. At 40° C. hydrogen uptake was accompanied by an exotherm. The temperature was allowed to rise to 75–83° C. The hydrogen uptake was complete after 90 minutes. The reactor was stirred an additional 45 minutes at this temperature and cooled to room temperature. The catalyst was removed by filtration through Celite®. After removal of the solvent at reduced pressure, 1165.5 g of the title compound (95.9%) was obtained as a crystalline solid melting at 142–143° C. (purity: >99.5% by HPLC).

EXAMPLE 3

Preparation of N-(5-amino-4-chloro-2-fluorophenyl) acetamide

In a 1 L autoclave, 23.25 g (0.1 mole) of N-(4-chloro-2-fluoro-5-nitrophenyl)acetamide and 1.2 g of Ni-catalyst were suspended under nitrogen in 500 mL of ethyl acetate. The autoclave was purged two times with nitrogen at 500 kPa (5 atmospheres) and once with hydrogen at 500 kPa (5 atmospheres). 500 kPa (5 atmospheres) of hydrogen was then applied and the reactor heated to 75–80° C. After 6 hours the autoclave was cooled to room temperature. The catalyst was filtered off and the solvent removed under reduced pressure. The solid was triturated with petroleum ether and filtered to give 18.9 g of the title compound as a crystalline solid melting at 142–143° C. (purity: 99.4% by HPLC).

EXAMPLE 4

Preparation of N-[4-chloro-5-[[(chloromethyl)sulfonyl]amino]-2-fluorophenyl]acetamide 1000 g of crude N-(5-amino4-chloro-2-fluorophenyl)acetamide (4.93 mol) which still contained 1 L of ethyl acetate was dissolved in 3900 g (49.3 mol) of pyridine at 20° C. To the yellow solution was added 845 g (5.42 mol) of chloromethanesulfonyl chloride at 20–30° C. over 1–2 hours. The solution was allowed to stir for 1 additional hour. 2300 g of pyridine were distilled off under reduced pressure at 40° C. To the remaining reaction mixture were added 5.3 L of water and 1.7 L of concentrated HCl (pH 3) whereupon the product precipitated. The slurry was cooled to 20° C. and filtered off. The filter cake was washed twice with 1300 mL of water. The product was dried in vacuo at 70° C. to yield 1500 g (92% purity) of the title compound as a solid melting at 210° C.

EXAMPLE 5

Preparation of N-(5-amino-2-chloro-4-fluorophenyl)-1-chloromethanesulfonamide 110.2 g of N-[4-chloro-5-[[(chloromethyl)sulfonyl]amino]-2-fluorophenyl]acetamide was suspended with stirring in 317 mL of 6 N NaOH solution. The mixture was heated to 50–55° C. whereupon the suspension turned into a solution. The reaction was monitored by HPLC. After 4 hours the solution was cooled to 30° C. and acidified to pH 8 by the addition of concentrated hydrochloric acid. 1 mL of dimethoxyethane was added to the suspension. Addition of more concentrated hydrochloric acid (155 mL total) was continued until pH 4 was reached and the precipitation was complete. The solid was filtered off and washed twice with 35 mL of water to yield, after drying, 93.4 g of yellow crystals (purity: 96% by HPLC).

25 g of water containing the crude product isolated above and 1 g of Celite® were suspended in 80 mL of toluene and heated to reflux. The suspension turned into a solution. Water was removed by azeotropic distillation. The hot mixture was filtered to remove the Celite®. The filtrate was allowed to come to room temperature over 3–4 hours and the resulting suspension was further cooled to 5° C. The crystalline solid was filtered off and dried to yield 13.2 g of the title compound as a solid melting at 105–107° C. (purity: 97–98%). The same recrystallization conditions can be applied to the crude product of Step 4 obtained from acidic hydrolysis.

EXAMPLE 6

Preparation of N-(5-amino-2-chloro4-fluorophenyl)-1-chloromethanesulfonamide 74.5 g of crude N-[4-chloro-5-[[(chloromethyl)sulfonyl]amino]-2-fluorophenyl]acetamide (purity: 90%) was suspended in 355 mL of 6 N hydrochloric acid and heated to 95° C. After 1.5 hours the suspension turned into a solution. The mixture was cooled to room temperature and 90 mL of a NaOH solution (50%) was added (pH 3). The precipitated product was filtered and washed with water to yield, after drying, 62.8 g of the title compound as yellow crystals (purity: 86.4% by HPLC) which could be further purified by recrystallization as described above in Example 5.

EXAMPLE 7

Preparation of 1-chloro-N-(2-chloro-4-fluoro-5-isocyanatophenyl)methanesulfonamide To a stirred solution of 218 g (2.2 mole) of phosgene in 0.6 L of methyl isobutyl ketone at 0° C. was added 546.2 g (2 mol) of N-(5-amino-2-chloro-4-fluorophenyl)-1-chloromethanesulfonamide dissolved in 2 L of methyl isobutyl ketone. During the addition (75 minutes) the temperature was kept between −3° C. and 3° C. The temperature of the solution was raised to 35° C. and 1 L of the solvent was distilled off under reduced pressure (11.0–11.5 kPa (110–115 mbar), maximum temperature: 60° C.). This isocyanate solution was used in the next step without further purification.

EXAMPLE 8

Preparation of (2R-cis)-1-[[[4-chloro-5-[[(chloromethylsulfonyl]amino]-2-fluorophenyl]amino]carbonyl]-4-hydroxy-2-pyrrolidinecarboxylic acid To a stirred solution of cis-4-hydroxy-D-proline (262 g, 2 mol) in 2 L of 1 N NaOH at 0° C. was added dropwise 1950 mL of a solution of 1-chloro-N-(2-chloro-4-fluoro-5-isocyanatophenyl)methanesulfonamide in methyl isobutyl ketone over 90 minutes. The temperature was kept between −3° C. and 5° C. The pH was maintained at 8–9 by the addition of 550 mL of 10% NaOH. Stirring was continued at this temperature for another hour at pH 8 and then the two-phase mixture was allowed to come to room temperature. 70 mL of concentrated HCl was added in order to lower the pH to 6.5. After stirring for 20 minutes, the phases were separated. Methyl isobutyl ketone was added to the aqueous phase and the solution was acidified with concentrated hydrochloric acid to pH 2. After addition of solid sodium chloride and vigorous stirring the organic layer was separated. The solvent was removed to yield 775 g (90%) of the title compound (purity: 95–97% by HPLC). $^1$H NMR (Me$_2$SO-d$_6$) δ12.4 (br s, 1H), 10.1 (br s, 1H), 8.2 (s, 1H), 7.7 (d, 1H), 7.5 (d, 1H), 5.1–5.0 (br s, 1H), 5.0–4.9 (s, 2H), 4.4 (m, 1H), 4.3 (m, 1H), 3.7–3.6 (m, 1H), 3.4–3.3 (m, 2H), 2.4–2.3 (m, 1H).

EXAMPLE 9

Preparation of (6R-trans)-1-chloro-N-[2-chloro-4-fluoro-5-(tetrahydro-6-hydroxy-1,3-dioxo-1H-pyrrolo[1,2-c]imidazol-2(3H)-yl)phenyl]methanesulfonamide 295.5 g (0.25 mol) of (2R-cis)-1-[[[4-chloro-5-[[(chloromethyl)sulfonyl]amino]-2-fluorophenyl]amino]carbonyl]-4-hydroxy-2-pyrrolidinecarboxylic acid was suspended in 150 g of methyl isobutyl ketone at room temperature. 12.75 g (0.125 mol) of concentrated sulfuric acid was added and the clear solution was heated to reflux. At 90° C. a precipitate appeared. After an additional 20 minutes of stirring at reflux the suspension was cooled to 0° C. and allowed to stir for 1 hour at this temperature. After filtration and drying at 60° C., 91.65 g (86.6%) of the title compound was obtained as beige crystals melting at 198–200° C. (purity: 97%).

EXAMPLE 10

Preparation of (6S-cis)-1-chloro-N-[2-chloro-4-fluoro-5-(6-fluorotetrahydro-1,3-dioxo-1H-pyrrolo[1,2-c]imidazol-2(3H)-yl)phenyl]methanesulfonamide In a Teflon® flask fitted with a Teflon®-lined condenser, thermocouple, and plastic addition tube, 30.9 g (75.0 mmol) of (6R-trans)-1-chloro-N-[2-chloro4-fluoro-5-(tetrahydro-6-hydroxy-1,3-dioxo-1H-pyrrolo[1,2-c]imidazol-2(3H)-yl)phenyl]methanesulfonamide was suspended in 150 mL of chlorobenzene. The mixture was heated to 130° C. and 16.8 g (75.3 mmol) of 1,1,2,3,3,3-hexafluoropropyldiethylamine (N. Ishikawa et al. *Bull. Chem. Soc. Japan* (1979) 52, 3377) was added over two minutes. The mixture was stirred for 10 minutes at 123–130° C., then another 1.6 g (7.2 mmol) of 1,1,2,3,3,3-hexafluoropropyldiethylamine was added all at once. After stirring for 10 minutes at 127–130° C., the mixture was cooled to 90° C. and vacuum (20 kPa, 150 mm Hg) was applied while cooling to 50° C. Then 30 mL of methanol was added and vacuum (20 kPa, 150 mm Hg) was applied for another 10 minutes while cooling to 35° C. The mixture was then cooled to 0° C. with an ice-water bath and 17.0 mL (15.5 g, 85 mmol) of dicyclohexylamine (DCHA) was added dropwise at 20–25° C. Then 150 mL of heptane was added dropwise. The solid precipitate was filtered, washed with chlorobenzene (twice with 30 mL), and dried under nitrogen to afford 37.17 g (83.3%) of the DCHA salt of (6S-cis)-1-chloro-N-[2-chloro-4-fluoro-5-(6-fluorotetrahydro-1,3-dioxo-1H-pyrrolo[1,2-c]imidazo-2(3H)-yl)phenyl]methanesulfonamide as an off-white powder.

After drying, 30.0 g (50.4 mmol) of the DCHA salt of (6S-cis)-1-chloro-N-[2-chloro4-fluoro-5-(6-fluorotetrahydro-1,3-dioxo-1H-pyrrolo[1,2-c]imidazo-2(3H)-yl)phenyl]methanesulfonamide was suspended in 90 mL of methanol, and 15.0 g of 20% sulfuric acid was added dropwise at 25–30° C. The mixture was stirred until crystallization began (seeding may be helpful), then 45 mL of water was added dropwise at 25–30° C. and the mixture was stirred to complete crystallization. The crystals were filtered, washed with 1:1 methanol-water until neutral, then dried under nitrogen to afford 17.12 g (82.0%) of the title compound as a white powder melting at 147–151° C. $^1$H NMR (CDCl$_3$): δ1.9–2.2 (m, 1H), 2.66 (m, 1H), 3.60 (dd, 1H), 4.09 (ddd, 1H), 4.46 (s, 2H), 4.61 (dd, 1H), 5.49 (d, J=1Hz, 1H), 7.32 (d, 1H), 7.65 (d, 1H).

EXAMPLE 11

Preparation of (2R-trans)-4-fluoro-2-pyrrolidinecarboxylic acid

A suspension of 65.0 g (0.50 mol) of cis4-hydroxy-D-proline in 1500 mL of methanol was cooled to 0° C. and 110 mL (179 g, 1.5 mol) of thionyl chloride was added dropwise at 0–5° C. The mixture was then allowed to warm to room temperature overnight. The volatiles were removed under reduced pressure and the residue was triturated with diethyl ether to afford 98.73 g of crude cis-4-hydroxy-D-proline methyl ester hydrochloride as a white solid.

This ester was added in portions to a stirred mixture of 1500 mL of 1 N aqueous sodium bicarbonate and 500 mL of dichloromethane at 0–5° C., then 80 mL (97 g, 0.69 mol) of benzoyl chloride was added dropwise at 0–5° C., and the mixture was stirred at room temperature overnight. The phases were separated and the aqueous phase was extracted with dichloromethane (twice with 250 mL). The organic phases were combined, dried over magnesium sulfate, and evaporated under reduced pressure. The residue was triturated with toluene to afford 112.98 g (90.7% from cis4-hydroxy-D-proline) of N-benzoyl-cis-4-hydroxy-D-proline methyl ester as a white powder.

The N-benzoyl-cis-4-hydroxy-D-proline methyl ester (112.98 g, 454 mmol) was dissolved in 200 mL of dichloromethane and this solution was added dropwise to a solution of 161 g (722 mmol) of 1,1,2,3,3,3-hexafluoropropyldiethylamine [N. Ishikawa et al. *Bull. Chem. Soc. Japan* (1979) 52 3377] in 800 mL of toluene at room temperature. The mixture was then stirred overnight at room temperature. The stirring was stopped, a lower oil layer was separated, and the upper layer was evaporated under reduced pressure to afford 160.7 g of a brown oil. This oil was suspended in 800 mL of 6 N hydrochloric acid and the mixture was refluxed for 1 hour, then cooled to room temperature. The mixture was washed with dichloromethane (200 mL, then twice with 100 mL) to remove benzoic acid, then with diethyl ether (200 mL), and the aqueous layer was evaporated to dryness under reduced pressure to afford crude trans-4-fluoro-D-proline hydrochloride as a brown solid, 61.50 g (79.9% from the protected hydroxyproline).

The crude trans-4-fluoro-D-proline hydrochloride was dissolved in 400 mL of ethanol by heating, then cooled to room temperature, treated with 5.0 g of charcoal, and filtered through Celite®, rinsing with ethanol (total 100 mL). To the filtrate was added 50 mL (42 g, 0.71 mol) of propylene oxide dropwise at room temperature. This mixture was stirred at room temperature overnight, then filtered, and the solids were washed with ethanol to afford 36.00 g (74.6%) of crude trans-fluoro-D-proline as a light yellow powder.

The crude trans-4-fluoro-D-proline (146.55 g) was dissolved in 200 mL of boiling water, 2.0 g of charcoal were added, and the mixture was filtered while hot through Celite®, rinsing with 90 mL of hot water. The solution was heated to reflux, 580 mL of ethanol was added slowly at reflux and the mixture was allowed to cool to room temperature overnight. The crystalline precipitate was then filtered, washed with 2:1 ethanol-water (total 100 mL), then with ethanol, and dried to afford 91.47 g of trans-4-fluoro-D-proline as off-white crystals melting at 258–260° C. with decomposition. $^1$H NMR (D$_2$O): δ1.9–2.2 (m, 1H), 2.45–2.65 (m, 1H), 3.3–3.6 (m, 2H), 4.20 (dd, 1H), 5.33 (d, J=52 Hz, 1H). Additional crops could be collected by concentration of the filtrates, but they would be of lesser purity.

EXAMPLE 12

Preparation of (2R-trans)-1-[[[4-chloro-5-[[(chloromethyl)sulfonyl]amino]-2-fluorophenyl]amino]carbonyl]-4-fluoro-2-pyrrolidinecarboxylic acid 1-chloro-N-(2-chloro-4-fluoro-5-isocyanatophenyl)methanesulfonamide (120 g, 401 mmol) was dissolved in 400 mL of dry tetrahydrofuran. 55.8 g (420 mmol) of (2R-trans)-4-fluoro-2-pyrrolidinecarboxylic acid was added in a single portion and the mixture was stirred overnight at room temperature. The mixture was then filtered and the tetrahydrofuran was evaporated under reduced pressure. The residue was dissolved in 800 mL of ethyl acetate, a solution of 86.0 g of sodium bicarbonate in 870 mL of water was added and then solid sodium chloride was added to saturate the aqueous layer. The aqueous layer was separated, washed with 250 mL of ethyl acetate, and then with diethyl ether (twice with 250 mL). The aqueous layer was then added slowly to a stirred mixture of 120 mL of concentrated hydrochloric acid, 240 mL of water, and 800 mL of tetrahydrofuran. Solid sodium chloride was then added to saturate the aqueous layer, the layers were separated, and the aqueous layer was extracted with 100 mL of tetrahydrofuran. The tetrahydrofuran layers were combined, dried over magnesium sulfate, and evaporated under reduced pressure to afford 173.43 g of the title compound as a glassy solid, suitable for use in the next step. $^1$H NMR (DMSO-d$_6$): δ2.0–2.3 (m, 1H), 2.5–2.6 (m, 1H), 3.66 (m, 1H), 3.86 (m, 1H), 4.97 (s, 2H), 5.40 (d, J=54 Hz, 1H), 7.52 (d, 1H), 7.66 (d, 1H), 8.48 (s, 1H), 10.10 (br s, 1H).

EXAMPLE 13

Preparation of (6S-cis)-1-chloro-N-[2-chloro-4-fluoro-5-(6-fluorotetrahydro-1,3-dioxo-1H-pyrrolo[1,2-c]imidazol-2(3H)-yl)phenyl]methanesulfonamide Crude (2R-trans)-1-[[[4-chloro-5-[[(chloromethyl)sulfonyl]amino]-2-fluorophenyl]amino]carbonyl]-4-fluoro-2-pyrrolidinecarboxylic acid (173.43 g) was suspended in 550 mL of dichloromethane and 0.65 mL (0.61 g, 8.4 mmol) of N,N-dimethylformamide was added, followed by the dropwise addition of 58 mL (95 g, 0.80 mol) of thionyl chloride at room temperature, and stirring was continued at room temperature. After 2.5 hours, the mixture became homogeneous. After 22 hours, the mixture was poured into 500 mL of ice-water, the layers were separated and the aqueous layer was extracted with dichloromethane (twice with 75 mL). The organic layers were combined, washed with saturated aqueous sodium bicarbonate (twice with 400 mL), dried over magnesium sulfate and evaporated under reduced pressure to afford 140.69 g of the crude title compound (84.7% yield from the isocyanate).

This crude product (140.69 g, 340 mmol) was dissolved in 680 mL of acetone at 0° C., and a solution of 71 mL (65 g, 0.36 mol) of dicyclohexylamine (DCHA) in 85 mL of acetone was added dropwise at 0–5° C. The mixture was stirred for 30 minutes at 0° C., then filtered, and the solids were washed with acetone at 0° C. and dried to provide 184.32 g of the DCHA salt of (6S-cis)-1-chloro-N-[2-chloro-4-fluoro-5-(6-fluorotetrahydro-1,3-dioxo-1H-pyrrolo[1,2-c]imidazol-2(3H)-yl)phenyl]methanesulfonamide. Two additional crops totaling 13.71 g were obtained by concentration of the filtrates.

The first crop of the DCHA salt of (6S-cis)-1-chloro-N-[2-chloro-4-fluoro-5-(6-fluorotetrahydro-1,3-dioxo-1H-pyrrolo[1,2-c]imidazol-2(3H)-yl)phenyl]methanesulfonamide (184.32 g) was suspended in 900 mL of dichloromethane at 0° C. and 500 mL of 10% sulfuric acid was added dropwise at 0–10° C. The mixture was allowed to warm to room temperature, the organic phase was separated, washed with 400 mL of water, then with 400 mL of brine, dried over magnesium sulfate and evaporated to afford 124.32 g of purified (6S-cis)-1-chloro-N-[2-chloro-4-fluoro-5-(6-fluorotetrahydro-1,3-dioxo-1H-pyrrolo[1,2-c]imidazol-2(3H)-yl)phenyl]methanesulfonamide as a white solid.

This solid was recrystallized by dissolving it in 373 mL of chlorobenzene at 125° C., allowing the solution to cool slowly to 70° C., then adding 373 mL of hexanes dropwise and allowing the mixture to cool to room temperature. The crystals were filtered, washed with 1:1 chlorobenzene-hexanes (200 mL total), then with hexanes, and dried to afford 115.60 g of crystalline (6S-cis)-1-chloro-N-[2-chloro-4-fluoro-5-(6-fluorotetrahydro-1,3-dioxo-1H-pyrrolo[1,2-c]imidazol-2(3H)-yl)phenyl]methanesulfonamide as a white powder melting at 168–170° C.

EXAMPLE 14

Preparation of 1,1,2,2-tetrafluoroethyldiethylamine 1,1,2,2-tetrafluoroethyldiethylamine is prepared by the addition of tetrafluoroethylene at pressures of up to 700 kPa (100 psig) to an agitated solution of diethylamine. Equipment used for this preparation consists of a one liter bomb in a barricaded rocker arm, on account of the explosive nature of tetrafluoroethylene at elevated pressures. The reaction is carried out between 25 and 91° C. The obtained crude product is fractionated at 14 kPa of pressure (100 mm Hg) to yield a liquid product having a boiling point between 70 and 90° C.

EXAMPLE 15

Preparation of (6R-trans)- and (6S-cis)-1-chloro-N-[2-chloro-4-fluoro-5-(6-fluorotetrahydro-1,3-dioxo-1H-pyrrolo[1,2-c]imidazol-2(3H)-yl)phenyl]methanesulfonamide 7 g of (6R-trans)-1-chloro-N-(2-chloro-4-fluoro-5-(tetrahydro-6-hydroxy-1,3-dioxo-H-pyrrolo[1,2-c]imidazol-2(3H)-yl)phenyl)methanesulfonamide was suspended in 60 mL of monochlorobenzene. After heating to 103° C. with agitation and a water reflux condenser, 4 g of the above prepared 1,1,2,2-tetrafluoroethyldiethylamine in 6 g of monochlorobenzene was added over 15 minutes. After a 10 minute period into the addition it was observed that the suspended solids began to dissolve. The mixture was maintained at 120° C. for an additional 35 minutes, then cooled and assayed by liquid chromatography which indicated 2% of the starting material remaining, 84% conversion to the desired product and a selectivity ratio of 13.611 between (6S-cis)- and (6R-trans)-1-chloro-N-[2-chloro-4-fluoro-5-(6-fluorotetrahydro-1,3-dioxo-1H-pyrrolo[1,2-c]imidazol-2(3H)-yl)phenyl]methanesulfonamide.

EXAMPLE 16

Preparation of (6S-cis)-1-chloro-N-[2-chloro-4-fluoro-5-(6-fluorotetrahydro-1,3-dioxo-1H-pyrrolo[1,2-c]imidazol-2(3H)-yl)phenyl]methanesulfonamide In a Teflon® flask, a suspension of (6R-trans)-1-chloro-N-[2-chloro4-fluoro-5-(tetrahydro-6-hydroxy-1,3-dioxo-1H-pyrrolo[1,2-c]imidazol-2(3H)-yl)phenyl]methanesulfonamide (8.24 g, assay 94.5% pure, 18.9 mmol) in 1,2-dichloroethane (40 mL) was heated to reflux and then 1,1,2,2-tetrafluoroethyldiethylamine (3.8 g, 26 mmol) was added over 1–2 minutes. Refluxing was continued for 1 hour, then 20 mL of the solvent was distilled out of the reaction mixture at atmospheric pressure. The reaction mixture was cooled to 50° C., 1-propanol (1 mL) was added, the pressure was reduced to about 20 kPa (150 mm Hg) for 10 minutes, and then the remaining solvent was distilled off at 55–60° C. at 20 kPa (150 mm Hg). More l-propanol (15 mL) was added at 60° C., then the mixture was cooled slowly to room temperature, and stirred overnight at room temperature to complete the crystallization. The mixture was filtered and the solids were rinsed with several portions of 1-propanol (10 mL total) and dried to afford 6.57 g (79.3% crude yield) of the title compound as a white powder melting at 166–168° C. (purity: 97.3% by HPLC).

EXAMPLE 17

Preparation of 1-chloro-N-(2-chloro-4-fluorophenyl)methanesulfonamide 72.8 g (0.5 mol) of 2-chloro-4-fluoroaniline were dissolved in 400 mL of toluene and cooled to 5–10° C., and then 79 g (0.53 mol) of chloromethylsulfonyl chloride were added slowly with stirring. The temperature was kept below 10–15° C. The mixture was then heated to 40° C. for 30 minutes and cooled again to 5–10° C. At this temperature, 101 g (1 mol) of triethylamine was added with stirring and cooling. After the addition was complete, the mixture was stirred at 40° C. for an additional 8 hours and then poured into 1050 mL of 6 N hydrochloric acid. The organic phase was separated and the aqueous phase was washed with toluene. The combined organic phases were poured with vigorous stirring into 12.5% sodium hydroxide solution. The basic aqueous phase was separated and the organic phase was washed with aqueous sodium hydroxide solution. The combined aqueous phases were treated with active carbon and filtered. 6 N hydrochloric acid was added with cooling until the pH was below 7. The precipitated product was filtered off, washed with water and dried to yield 96.8 g (75%) of the title compound as a solid melting at 83–85° C.

EXAMPLE 18

Preparation of N-(2-chloro-4-fluorophenyl)-N-[(chloromethyl)sulfonyl]acetamide 77.5 g (0.3 mol) of 1-chloro-N-(2-chloro-4-fluorophenyl)methanesulfonamide were dissolved in 204.2 g (2 mol) of acetic anhydride and refluxed for 4 hours. The excess acetic anhydride was distilled off under reduced pressure at 100° C. To the still hot residue was added ethanol with stirring and the product precipitated (seeding may aid in crystallization). The crude product was filtered off and washed with cold ethanol and dried to yield 72 g (80%) of the title compound as a solid melting at 89–92° C.

EXAMPLE 19

Preparation of N-(2-chloro-4-fluoro-5-nitrophenyl)-N-[(chloromethyl)sulfonyl]acetamide 30 g (0.1 mol) of N-(2-chloro-4-fluorophenyl)-N-[(chloromethyl)sulfonyl]acetamide was dissolved in a mixture of 150 mL of concentrated sulfuric acid and 50 mL of 30% oleum with stirring. The mixture was cooled to 0–5° C. and 9.2 mL of the nitrating agent, made from equal volumes of concentrated sulfuric acid and fuming nitric acid, was added slowly keeping the temperature below 5° C. Another 50 mL of oleum and 30 g of the starting material were then added, followed by the further dropwise addition of 9.2 mL of the nitrating agent, allowing the mixture to warm up to 10° C. The mixture was stirred for an additional 40 minutes at 10–15° C. and poured with vigorous stirring onto ice. The precipitated yellow solid was filtered off, washed with water and dried to yield 63.5 g (92%) of the title compound as a solid, which was recrystallized from ethyl acetate, melting at 183–187° C.

EXAMPLE 20

Preparation of N-(5-amino-2-chloro-4-fluorophenyl)-N-[(chloromethyl)sulfonyl]acetamide 65.7 g (0.19 mol) of N-(2-chloro-4-fluoro-5-nitrophenyl)-N-[(chloromethyl)sulfonyl]acetamide were dissolved in 1200 mL of ethanol and transferred into an autoclave. 2.5 g of an iridium catalyst (5% on carbon) were added and the apparatus was purged with nitrogen and hydrogen, respectively. A hydrogen pressure of 2,000 kPa (20 atmospheres) was applied and the mixture was heated to 80° C. After 4 hours the hot reaction mixture was filtered and cooled to room temperature whereas some of the product precipitated. The crystals were filtered off and the mother liquor was concentrated and cooled. The precipitates were combined and dried to yield 41.9 g (70.2%) of the title compound as a solid melting at 176–180° C.

EXAMPLE 21

Preparation of N-(5-amino-2-chloro-4-fluorophenyl)-1-chloromethanesulfonamide 3 g (0.0095 mol) of N-(5-amino-2-chloro-4-fluorophenyl)-N-[(chloromethyl)sulfonyl]acetamide were dissolved in 30 mL of ethanol and 30 mL of 25% sodium hydroxide solution. The mixture was stirred for 3 hours at 50° C. and then cooled to room temperature. 6 N hydrochloric acid was added with stirring and cooling until the solution had a pH of 5–6. The suspension was further cooled to 0–5° C., filtered, washed with water and dried to yield 2.4 g (92%) of the title compound as a solid melting at 103.5–105.5° C. Recrystallization from toluene raised the melting point to 105–106° C.

EXAMPLE 22

Preparation of 1-chloro-N-(4-fluoro-3-nitrophenyl)methanesulfonamide 20 g of 4-fluoro-3-nitroaniline (128 mmol) was dissolved in a mixture of 200 mL of dichloromethane and 40 mL of pyridine. To this solution was added 21 g (140 mmol) of chloromethylsulfonyl chloride dropwise at 20–30° C., followed by the addition of 3.21 g of dimethylaminopyridine. The solution was stirred for an additional 3 hours. The reaction mixture was transferred into a separatory funnel and washed sequentially with water (twice with 25 mL), 5% HCl (twice with 25 mL), and water (25 mL). The organic phase was separated, dried (MgSO$_4$), filtered and concentrated under reduced pressure to yield 32 g (93%) of the title compound as a solid melting at 112–113° C.

EXAMPLE 23

Preparation of N-(3-amino-4-fluorophenyl)-1-chloromethanesulfonamide

A mixture of 12.5 g of iron powder (223 mmol) and 16 mL of an aqueous solution of acetic acid (8%) was heated to 80° C., and a solution of 6 g of I -chloro-N-(4-fluoro-3-nitrophenyl)methanesulfonamide (22.3 mmol) in 20 mL of glacial acetic acid and 22 mL ethyl acetate was added dropwise to the mixture. After heating for 1.5 h the reaction mixture was filtered through a pad of Celite® and washed with 200 mL of ethyl acetate and water (twice with 25 mL). The organic phase was separated, dried (MgSO$_4$), filtered and concentrated under reduced pressure to yield 5 g (94%) of the title compound as a solid melting at 128–129° C.

EXAMPLE 24

Preparation of N-(5-amino-2-chloro-4-fluorophenyl)-1-chloromethanesulfonamide

A mixture of N-(3-amino-4-fluorophenyl)-1-chloromethanesulfonamide (4.42 g, 18.5 mmol), N-chlorosuccinimide (2.47 g) in 50 mL of anhydrous dimethylformamide was heated to 50° C. for 1.5 hours. The reaction mixture was diluted with 200 mL of ethyl acetate and washed with water (twice with 50 mL). The organic phase was separated, dried (MgSO$_4$), and concentrated under reduced pressure to yield 4.15 g (82%) of the title compound. Purification by flash chromatography provided a solid melting at 107–108° C.

We claim:

1. A compound of Formula 3,

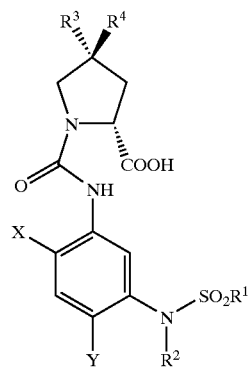

wherein
X is H;
Y is F or Cl;
$R^1$ is $C_1$–$C_3$ haloalkyl, $C_2$–$C_4$ alkoxyalkyl; $C_2$–$C_6$ haloalkoxyalkyl or $C_2$–$C_6$ cyanoalkyl;
$R^2$ is H, $C_1$–$C_4$ alkyl, $C_1$–$C_4$ haloalkyl, $C_3$–$C_4$ alkenyl, $C_3$–$C_4$ alkynyl, $C_2$–$C_4$ alkoxyalkyl, $C_2$–$C_4$ alkylcarbonyl or $C_2$–$C_4$ alkoxycarbonyl;
$R^3$ is H or OH; and
$R^4$ is H, F or Cl;
provided that when $R^3$ is H then $R^4$ is F or Cl and when $R^3$ is OH then $R^4$ is H.

2. A compound of Formula 3,

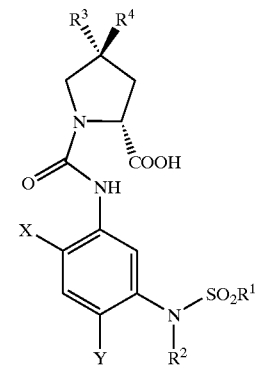

wherein
X is H, F or Cl;
Y is F or Cl;
$R^1$ is $C_2$–$C_4$ alkoxyalkyl;
$R^2$ is H, $C_1$–$C_4$ alkyl, $C_1$–$C_4$ haloalkyl, $C_3$–$C_4$ alkenyl, $C_3$–$C_4$ alkynyl, $C_2$–$C_4$ alkoxyalkyl, $C_2$–$C_4$ alkylcarbonyl or $C_2$–$C_4$ alkoxycarbonyl;
$R^3$ is H or OH; and
$R^4$ is H, F or Cl;
provided that when $R^3$ is H then $R^4$ is F or Cl and when $R^3$ is OH then $R^4$ is H.

3. The compound as claimed in claim 2, wherein X is F.
4. The compound as claimed in claim 2, wherein X is Cl.
5. The compound as claimed in claim 1, wherein Y is F.
6. The compound as claimed in claim 1, wherein Y is Cl.
7. The compound as claimed in claim 1, wherein $R^1$ is $C_1$–$C_3$ haloalkyl.
8. A compound of claim 1, wherein $R^1$ is $C_1$–$C_3$ haloalkyl; and $R^2$ is H.
9. A compound of Formula 3,

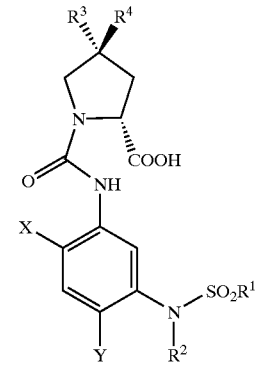

wherein
X is H, F or Cl;
Y is F or Cl;
$R^1$ is $C_2$–$C_6$ haloalkoxyalkyl;
$R^2$ is H, $C_1$–$C_4$ alkyl; $C_1$–$C_4$ haloalkyl, $C_3$–$C_4$ alkenyl, $C_3$–$C_4$ alkynyl, $C_2$–$C_4$ alkoxyalkyl, $C_2$–$C_4$ alkylcarbonyl or $C_2$–$C_4$ alkoxycarbonyl;

$R^3$ is H or OH; and
$R^4$ is H, F or Cl;
provided that when $R^3$ is H then $R^4$ is F or Cl and when $R^3$ is OH then $R^4$ is H.

10. A compound of Formula 3,

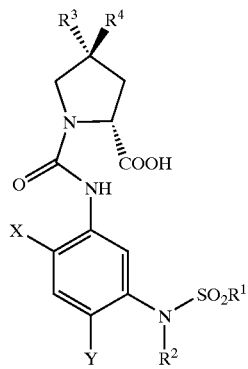

wherein
$X$ is H, F or Cl;
$Y$ is F or Cl;
$R^1$ is $C_2$–$C_6$ cyanoalkyl;
$R^2$ is H, $C_1$–$C_4$ alkyl, $C_1$–$C_4$ haloalkyl, $C_3$–$C_4$ alkenyl, $C_3$–$C_4$ alkynyl, $C_2$–$C_4$ alkoxyalkyl, $C_2$–$C_4$ alkylcarbonyl or $C_2$–$C_4$ alkoxycarbonyl;
$R^3$ is H or OH; and
$R^4$ is H, F or Cl;
provided that when $R^3$ is H then $R^4$ is F or Cl and when $R^3$ is OH then $R^4$ is H.

11. The compound as claimed in claim 1, wherein $R^2$ is H.

12. The compound as claimed in claim 1, wherein $R^2$ is $C_1$–$C_4$ alkyl.

13. A compound of Formula 3,

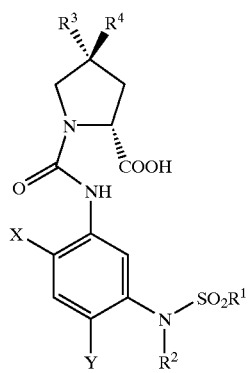

wherein
$X$ is H, F or Cl;
$Y$ is F or Cl;
$R^1$ is $C_1$–$C_3$ haloaklkyl, $C_2$–$C_4$ alkoxyalkyl; $C_2$–$C_6$ haloalkoxyalkyl or $C_2$–$C_6$ cyanoalkyl;
$R^2$ is $C_1$–$C_4$ haloalkyl;
$R^3$ is H or OH; and
$R^4$ is H, F or Cl;
provided that when $R^3$ is H then $R^4$ is F or Cl and when $R^3$ is OH then $R^4$ is H.

14. A compound of Formula 3,

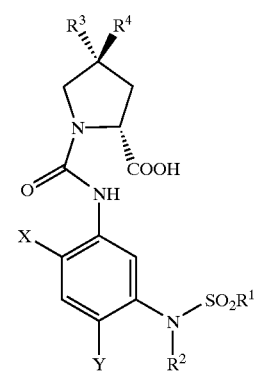

wherein
$X$ is H, F or Cl;
$Y$ is F or Cl;
$R^1$ is $C_1$–$C_3$ haloaklkyl, $C_2$–$C_4$ alkoxyalkyl; $C_2$–$C_6$ haloalkoxyalkyl or $C_2$–$C_6$ cyanoalkyl;
$R^2$ is $C_3$–$C_4$ alkenyl;
$R^3$ is H or OH; and
$R^4$ is H, F or Cl;
provided that when $R^3$ is H then $R^4$ is F or Cl and when $R^3$ is OH then $R^4$ is H.

15. A compound of Formula 3, wherein
$X$ is H, F or Cl;
$Y$ is F or Cl;
$R^1$ is $C_1$–$C_3$ haloaklkyl, $C_2$–$C_4$ alkoxyalkyl; $C_2$–$C_6$ haloalkoxyalkyl or $C_2$–$C_6$ cyanoalkyl;
$R^2$ is $C_3$–$C_4$ alkynyl;
$R^3$ is H or OH; and
$R^4$ is H, F or Cl;
provided that when $R^3$ is H then $R^4$ is F or Cl and when $R^3$ is OH then $R^4$ is H.

16. A compound of Formula 3,

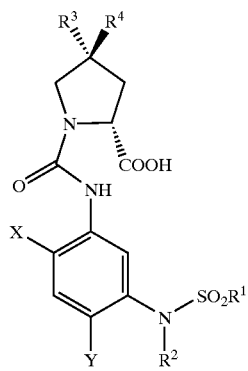

wherein

X is H, F or Cl;

Y is F or Cl;

$R^1$ is $C_1-C_3$ haloaklkyl, $C_2-C_4$ alkoxyalkyl; $C_2-C_6$ haloalkoxyalkyl or $C_2-C_6$ cyanoalkyl;

$R^2$ is $C_2-C_4$ alkoxyalkyl;

$R^3$ is H or OH; and $R^4$ is H, F or Cl;

provided that when $R^3$ is H then $R^4$ is F or Cl and when $R^3$ is OH then $R^4$ is H.

17. A compound of Formula 3,

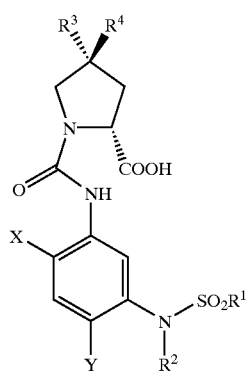

wherein

X is H, F or Cl;

Y is F or Cl;

$R^1$ is $C_1-C_3$ haloaklkyl, $C_2-C_4$ alkoxyalkyl; $C_2-C_6$ haloalkoxyalkyl or $C_2-C_6$ cyanoalkyl;

$R^2$ is $C_2-C_4$ alkylcarbonyl;

$R^3$ is H or OH; and $R^4$ is H, F or Cl;

provided that when $R^3$ is H then $R^4$ is F or Cl and when $R^3$ is OH then $R^4$ is H.

18. A compound of Formula 3,

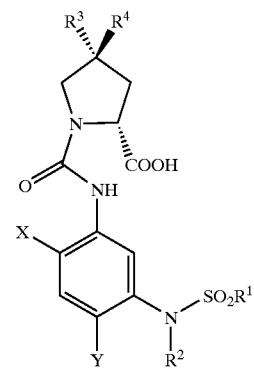

wherein

X is H, F or Cl;

Y is F or Cl;

$R^1$ is $C_1-C_3$ haloaklkyl, $C_2-C_4$ alkoxyalkyl; $C_2-C_6$ haloalkoxyalkyl or $C_2-C_6$ cyanoalkyl;

$R^2$ is $C_2-C_4$ alkoxycarbonyl;

$R^3$ is H or OH; and $R^4$ is H, F or Cl;

provided that when $R^3$ is H then $R^4$ is F or Cl and when $R^3$ is OH then $R^4$ is H.

19. A compound of Formula 3,

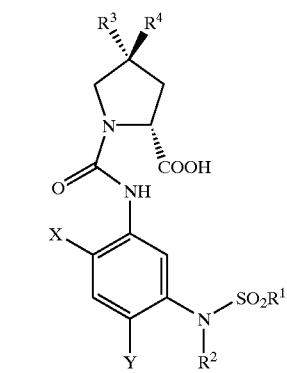

wherein

X is H, F or Cl;

Y is F or Cl;

$R^1$ is $C_1-C_3$ haloaklkyl, $C_2-C_4$ alkoxyalkyl; $C_2-C_6$ haloalkoxyalkyl or $C_2-C_6$ cyanoalkyl;

$R^2$ is H, $C_1-C_4$ alkyl, $C_1-C_4$ haloalkyl, $C_3-C_4$ alkenyl, $C_3-C_4$ alkynyl, $C_2-C_4$ alkoxyalkyl, $C_2-C_4$ alkylcarbonyl or $C_2-C_4$ alkoxycarbonyl;

$R^3$ is H; and $R^4$ is F or Cl.

20. The compound as claimed in claim 1, wherein $R^3$ is OH.

21. The compound as claimed in claim 1, wherein $R^4$ is H.

22. A compound of Formula 3,

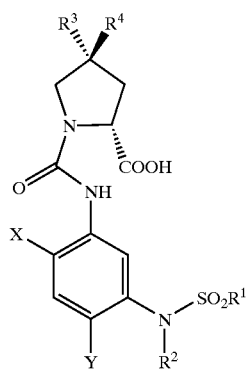

wherein
X is H, F or Cl;
Y is F or Cl;
R$^1$ is C$_1$–C$_3$ haloaklkyl, C$_2$–C$_4$ alkoxyalkyl; C$_2$–C$_6$ haloalkoxyalkyl or C$_2$–C$_6$ cyanoalkyl;
R$^2$ is H, C$_1$–C$_4$ alkyl, C$_1$–C$_4$ haloalkyl, C$_3$–C$_4$ alkenyl, C$_3$–C$_4$ alkynyl, C$_2$–C$_4$ alkoxyalkyl, C$_2$–C$_4$ alkylcarbonyl or C$_2$–C$_4$ alkoxycarbonyl;
R$^3$ is H; and
R$^4$ is F.

23. A compound of Formula 3,

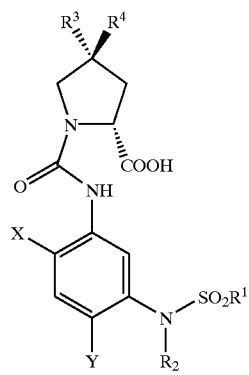

wherein
X is H, F or Cl;
Y is F or Cl;
R$^1$ is C$_1$–C$_3$ haloaklkyl, C$_2$–C$_4$ alkoxyalkyl; C$_2$–C$_6$ haloalkoxyalkyl or C$_2$–C$_6$ cyanoalkyl;
R$^2$ is H, C$_1$–C$_4$ alkyl, C$_1$–C$_4$ haloalkyl, C$_3$–C$_4$ alkenyl, C$_3$–C$_4$ alkynyl, C$_2$–C$_4$ alkoxyalkyl, C$_2$–C$_4$ alkylcarbonyl or C$_2$–C$_4$ alkoxycarbonyl;
R$^3$ is H; and
R$^4$ is Cl.

24. A process for preparing a compound of Formula 3

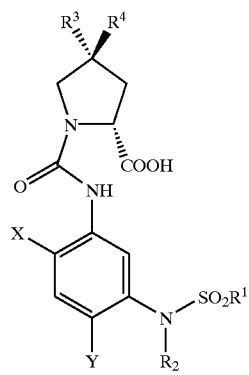

comprising a reaction of a compound of Formula 5

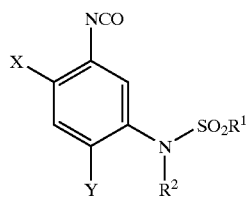

with a compound of Formula 4

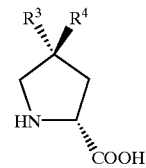

wherein
X is H, F or Cl;
Y is F or Cl;
R$^1$ is C$_1$–C$_3$ haloalkyl, C$_2$–C$_4$ alkoxyalkyl C$_2$–C$_4$ haloalkoxyalkyl or C$_2$–C$_6$ cyanoalkyl;
R$^2$ is H, C$_1$–C$_4$ alkyl, C$_1$–C$_4$ haloalkyl, C$_3$–C$_4$ alkenyl, C$_3$–C$_4$ alkynyl, C$_2$–C$_4$ alkoxyalkyl, C$_2$–C$_4$ alkylcarbonyl or C$_2$–C$_4$ alkoxycarbonyl;
R$^3$ is H or OH; and
R$^4$ is H, F or Cl;
provided that when R$^3$ is H then R$^4$ is F or Cl and when R$^3$ is OH then R$^4$ is H.

* * * * *